(12) United States Patent
March et al.

(10) Patent No.: US 10,143,709 B2
(45) Date of Patent: Dec. 4, 2018

(54) USE OF ASC AND ASC-CM TO TREAT ARDS, SARS, AND MERS

(71) Applicant: Indiana University Research and Technology Corp., Indianapolis, IN (US)

(72) Inventors: Keith March, Carmel, IN (US); Natalia Bogatcheva, Westfield, IN (US)

(73) Assignees: Indiana University Research and Technology Corporation, Indianapolis, IN (US); The United States of America Department of Veteran Affairs As Represented By The Technology Transfer Program, Washington, DC (US)

( * ) Notice: Subject to any disclaimer, the term of this patent is extended or adjusted under 35 U.S.C. 154(b) by 247 days.

(21) Appl. No.: 14/705,895

(22) Filed: May 6, 2015

(65) Prior Publication Data

US 2015/0320801 A1 Nov. 12, 2015

Related U.S. Application Data

(60) Provisional application No. 61/989,459, filed on May 6, 2014, provisional application No. 62/077,824, filed on Nov. 10, 2014.

(51) Int. Cl.
*A61K 35/28* (2015.01)
(52) U.S. Cl.
CPC ................................... *A61K 35/28* (2013.01)

(58) Field of Classification Search
None
See application file for complete search history.

(56) References Cited

PUBLICATIONS dos Santos et al., Cell Therapy in Acute Lung Injury, Pulmao RJ 2011; 20(1): 64-68.*
Ionescu et al., Stem cell conditioned medium improves acute lung injury in mice: in vivo evidence for stem cell paracrine action, NCBI (2012).*
Zheng et al., Treatment of acute respiratory distress syndrom with allogeneic adipose-derived mesenchymal stem cells: a randomized, placebo-controlled pilot study, Respiratory Research 2014, 15:39.*

* cited by examiner

*Primary Examiner* — Kortney L. Klinkel
*Assistant Examiner* — Stephen M Chong
(74) *Attorney, Agent, or Firm* — Faegre Baker Daniels LLP

(57) ABSTRACT

Disclosed herein is that the systemic administration of ASC conditioned media diminished LPS-induced lung injury by inhibiting epithelial permeability, neutrophil inflammatory response, and secretion of pro-inflammatory TNFα. It is also shown that ARDS lung is able to retain IV-delivered ASC for a substantial amount of time, with no evidence of the significant cell distribution to other organs at this time point. These findings provide optimization of cell-based and cell-free therapy for the treatment of ARDS, including occurrences of ARDS caused by upper respiratory tract infections such as SARS and MERS.

21 Claims, 53 Drawing Sheets

USE OF ASC AND ASC-CM TO TREAT ARDS, SARS, AND MERS

PRIORITY CLAIM

This application claims the benefit of U.S. Provisional Application No. 61/989,459 filed on May 6, 2014, and U.S. Provisional Application No. 62/077,824 filed on Nov. 10, 2014, the entire disclosures of both of which are hereby expressly incorporated by reference herein.

FIELD OF THE INVENTION

Aspects of the disclosure relate to using ASC and media or portions of media recovered from the incubation of ASC to treat disease and conditions such as ARDS, SARS, AND MERS.

BACKGROUND AND SUMMARY

Adult Respiratory Distress Syndrome (ARDS) is a serious pathological condition resulting in pulmonary failure, and therefore requiring patient hospitalization and admission to the critical care unit (1, 2). ARDS can be triggered by a variety of pulmonary and non-pulmonary causes, such as pneumonia, aspiration of gastric content and lung contusion, but also sepsis, burn, multiple trauma, and acute pancreatitis (3). ARDS is also the proximal cause of morbidity in a large percentage of patients who succumb to upper respiratory tract infections such as Severe Acute Respiratory Syndrome (SARS) caused by coronavirus SARS-CoV and Middle East Respiratory Syndrome (MERS) thought to be caused by coronavirus MERS-CoV.

Pathogenesis of ARDS includes inflammation of the lung parenchyma, infiltration of neutrophils into the airspaces, oxidative stress, disruption of the endothelial and epithelial barriers, damage to the epithelial lining and subsequent lung fibrosis. Despite the fact that the mechanisms contributing to the pulmonary failure are well delineated, more than 20 years of clinical trials show that approaches aiming at the separate components of pathogenesis fail to improve mortality (4). As of now, treatment remains primarily supportive and consists of the patient oxygenation with the lung protective ventilation strategy, and the tight control over the patient's fluid balance. Failure to alleviate ARDS with the numerous pharmacological and non-pharmacological strategies shaped a request for a novel complex therapy, which would not only limit the pathogenic mechanisms of ARDS but also facilitate lung repair (5, 6). Stem cell therapy seems to address this request for a multi-directional therapeutic action, as stem cells were shown to exert both anti-inflammatory and pro-angiogenic activity.

Some embodiments of the present disclosure include methods of treating ARDS in vivo by intravenously administering Adult Stem Cell Condition Media (ASC-CM). In some embodiments treating a patient in need thereof with ASC-CM alleviates ARDS in vivo, and reduces the mortality of currently incurable (as well as curable) diseases with significant mortality due to ARDS, caused by respiratory infections such as MERS/SARS. In some embodiments ASC and or ASC-CM and their effects include the limitation of acute kidney injury which may occur in MERS/SARS due to cytokine storm as well as hypoxia due to ARDS itself. In endotoxin-induced model of ARDS, it has been shown that ASC as well as ASC-CM diminishes lung histopathologic changes, namely the extravasation of neutrophils (inflammation) and Red Blood Cells (hemorrhage) into lung parenchyma and airspaces, and thickening of the alveolar wall. ASC-CM also inhibits endotoxin-induced increase in protein content in bronchoalveolar lavage, indicative of epithelial barrier dysfunction. It reduces endotoxin-induced release of pro-inflammatory cytokine Tumor Necrosis Factor alpha. It compromises the ability of lavage neutrophils to generate Reactive Oxygen Species, harmful to endothelial and epithelial barrier, and epithelial cell viability. In vitro, ASC-CM strengthens the ability of endothelial monolayers to counteract peroxide-induced barrier dysfunction. These data taken together clearly indicate that ASC-CM suppresses inflammation and barrier hyperpermeability, two key pathological mechanisms contributing to the development of lung edema in ARDS.

In some embodiments, ASC isolated from subcutaneous fat of the patient (frozen or freshly isolated) are expanded in the tissue culture flask/dish. ASC are grown until 30-90% confluent and incubated with growth media or basal media for 24-72 h. Collected media can be used as is, frozen, or concentrated using 3 kDa or higher cut-off filters. It has been found that the fractions larger than 50-100 kiloDaltons possess the greatest amount of activity, which is consistent with large molecules/complexes, or indeed exosomes bearing the therapeutic effect. In some embodiments, conditioned media ("CM") is obtained and manipulated (in some embodiments fractionated) under sterile conditions to allow injection into patients with lifer-threatening manifestation of MERS/SARS.

In some embodiments, ASC-CM was tested in a mouse model of endotoxin/LPS-induced ARDS. In this model, LPS was instilled directly into lungs to mimic gram-negative pneumonia. ASC-CM was injected intravenously 4 h after LPS instillation. At this time point, mice experienced hypothermic shock, and their lungs already showed the signs of neutrophil infiltration (inflammation). This model allowed for determining the effect of ASC-CM on ongoing ARDS development. At both 24 and 48 h post-injection, histopathologic changes of the lung are markedly suppressed in mice which received ASC-CM. At 48 h, the effect on protein extravasation in bronchoalveolar lavage, and tumor necrosis factor alpha content was evident. Lavage neutrophils from mice receiving ASC-CM displayed lessen ROS generation in response to LPS. In vitro data showed that pre-incubation of endothelial monolayers with ASC-CM suppresses peroxide-induced barrier dysfunction. One of skill in the art could test ASC-CM in a rodent models of lung contusion-induced ARDS, as well as infectious models related to MERS. The findings may be reproducible in an ovine model of LPS-induced ARDS.

Some embodiments include methods for treating a patient, comprising the step of: administering at least one therapeutically effective dose of ASC or ASC-CM to a patient, wherein the patient is afflicted with ARDS and wherein the patient is a human or an animal.

Some embodiments include methods for treating a patient, comprising the step of: administering at least one therapeutically effective dose of ASC or ASC-CM to a patient, wherein the patient is afflicted with ARDS and wherein the patient is a human or an animal, wherein ARDS is caused by an upper respiratory tract infection caused by coronavirus SARS-CoV or by coronavirus MERS-CoV.

Some embodiments include methods for treating a patient, comprising the step of: administering at least one therapeutically effective dose of ASC or ASC-CM to a patient, wherein the patient is afflicted with ARDS and wherein the patient is a human or an animal, wherein ARDS is caused by an upper respiratory tract infection caused by coronavirus SARS-CoV or by coronavirus MERS-CoV, where the therapeutically effective dose of ASC or ASC-CM is administered intravenously.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of ASC-CM, the ASC-CM comprising material have a molecular weight of greater than about 10,000 Daltons, 20,000 Daltons, 30,000 Daltons, 40,000 Daltons, 50,000 Daltons, 60,000 Daltons, 70,000 Daltons, 80,000 Daltons, 90,000 Daltons, 100,000 Daltons, or 150,000 Daltons.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of a fraction of ASC-CM, comprised of exosomes.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of a fraction of ASC-CM, comprised of exosomes concentrated by any of filtration, centrifugation, or precipitation and resuspension.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of a fraction of ASC-CM, comprised of exosomes, wherein the ASC-CM is administered intravenously or by aspirating the material into at least one lung of the patient.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of a fraction of ASC-CM, comprised of exosomes concentrated by any of filtration, centrifugation, or precipitation and resuspension, wherein the ASC-CM is administered intravenously or by aspirating the material into at least one lung of the patient.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the ASC-CM comprising material have a molecular weight of greater than about 10,000 Daltons, 20,000 Daltons, 30,000 Daltons, 40,000 Daltons, 50,000 Daltons, 60,000 Daltons, 70,000 Daltons, 80,000 Daltons, 90,000 Daltons, 100,000 Daltons, or 150,000 Daltons is administered intravenously.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the ASC-CM comprising material have a molecular weight of greater than about 10,000 Daltons, 20,000 Daltons, 30,000 Daltons, 40,000 Daltons, 50,000 Daltons, 60,000 Daltons, 70,000 Daltons, 80,000 Daltons, 90,000 Daltons, 100,000 Daltons, or 150,000 Daltons is administered by aspirating the material into at least one lung of the patient.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the ASC-CM comprising material have a molecular weight of greater than about 10,000 Daltons, 20,000 Daltons, 30,000 Daltons, 40,000 Daltons, 50,000 Daltons, 60,000 Daltons, 70,000 Daltons, 80,000 Daltons, 90,000 Daltons, 100,000 Daltons, or 150,000 Daltons is administered intravenously, wherein the dose of ASC-CM administered intravenously is about 0.1 ml/kg to about 2.0 ml/kg, of 100× concentrate of ASC-CM, preferably about 0.5 ml/kg to about 1.0 ml/kg, of 100× concentrate of ASC-CM.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of a fraction of ASC-CM, comprised of exosomes, wherein the dose of ASC-CM administered intravenously is about 0.1 ml/kg to about 2.0 ml/kg, of 100× concentrate of ASC-CM, preferably about 0.5 ml/kg to about 1.0 ml/kg, of 100× concentrate of ASC-CM.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of a fraction of ASC-CM, comprised of exosomes concentrated by any of filtration, centrifugation, or precipitation and resuspension, wherein the dose of ASC-CM administered intravenously is about 0.1 ml/kg to about 2.0 ml/kg, of 100× concentrate of ASC-CM, preferably about 0.5 ml/kg to about 1.0 ml/kg, of 100× concentrate of ASC-CM.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the dose of ASC administered intravenously is about $1 \times 10^6$ cells/kg to about $1 \times 10^8$ cells/kg, preferably about $1 \times 10^7$ cells/kg.

Some embodiments include methods for treating a patient, comprising the step of: administering at least one therapeutically effective dose of ASC or ASC-CM to a patient, wherein the patient is afflicted with ARDS and wherein the patient is a human or an animal, wherein ARDS is caused by an upper respiratory tract infection caused by coronavirus SARS-CoV or by coronavirus MERS-CoV, wherein the dose of ASC administered intravenously is about $1 \times 10^6$ cells/kg to about $1 \times 10^8$ cells/kg, preferably about $1 \times 10^7$ cells/kg.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of ASC-CM, the ASC-CM comprising material have a molecular weight of greater than about 10,000 Daltons, 20,000

Daltons, 30,000 Daltons, 40,000 Daltons, 50,000 Daltons, 60,000 Daltons, 70,000 Daltons, 80,000 Daltons, 90,000 Daltons, 100,000 Daltons, or 150,000 Daltons, further comprising the step of formulating ASC-CM material to avoid heat sensitivity.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of ASC-CM, the ASC-CM comprising material have a molecular weight of greater than about 10,000 Daltons, 20,000 Daltons, 30,000 Daltons, 40,000 Daltons, 50,000 Daltons, 60,000 Daltons, 70,000 Daltons, 80,000 Daltons, 90,000 Daltons, 100,000 Daltons, or 150,000 Daltons, further comprising the step of formulating ASC-CM material to avoid exosome sensitivity.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of a fraction of ASC-CM, comprised of exosomes, further comprising the step of formulating ASC-CM material to avoid heat sensitivity.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of a fraction of ASC-CM, comprised of exosomes, further comprising the step of formulating ASC-CM material to avoid exosome sensitivity.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of a fraction of ASC-CM, comprised of exosomes concentrated by any of filtration, centrifugation, or precipitation and resuspension, further comprising the step of formulating ASC-CM material to avoid heat sensitivity.

Some embodiments include methods for treating a patient, comprising the step of: administering at least one therapeutically effective dose of ASC or ASC-CM to a patient, wherein the patient is afflicted with ARDS and wherein the patient is a human or an animal, wherein the patient is administered a therapeutically effective dose of a fraction of ASC-CM, comprised of exosomes concentrated by any of filtration, centrifugation, or precipitation and resuspension, further comprising the step of formulating ASC-CM material to avoid exosome sensitivity.

CM (ASC-CM, white bars), and then stimulated with vehicle or 1 ng/ml TNF-α (4 h).

Figure 36:
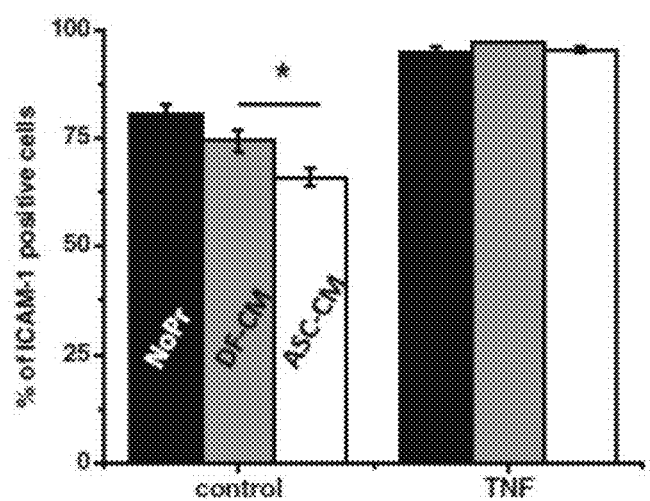

FIG. 36. Bar graph showing % of ICAM-1 positive cells in HPAEC that were pretreated with vehicle control (NoPr, black bars), NHCF-CM (DF-CM, grey bars), and hASC-CM (ASC-CM, white bars), and then stimulated with vehicle or 1 ng/ml TNF-α (4 h).

Figure 37:
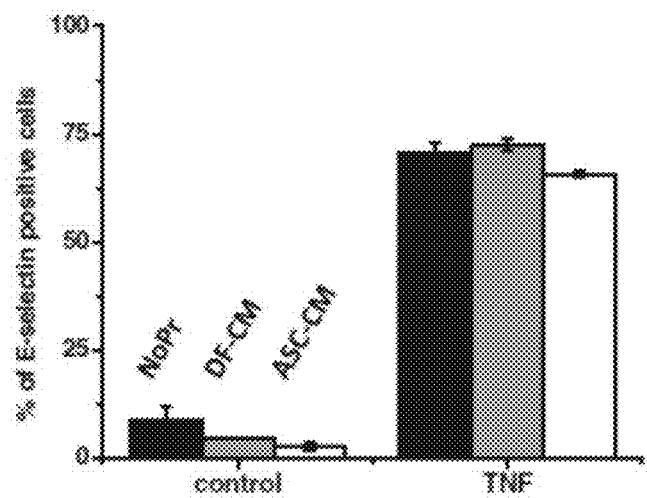

FIG. 37. Bar graph showing % of E-selectin positive cells in HPAEC that were pretreated with vehicle control (NoPr, black bars), NHCF-CM (DF-CM, grey bars), and hASC-CM (ASC-CM, white bars), and then stimulated with vehicle or 1 ng/ml TNF-α (4 h).

Figure 38:
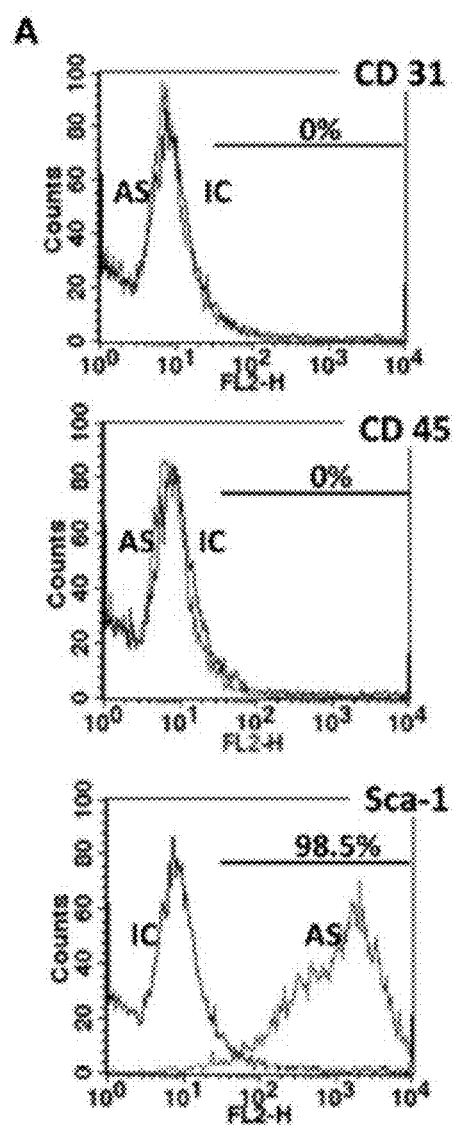

FIG. 38. Graph showing surface marker expression of mASC (IC-isotype controls and AS-antigen-specific antibodies).

Figure 39:
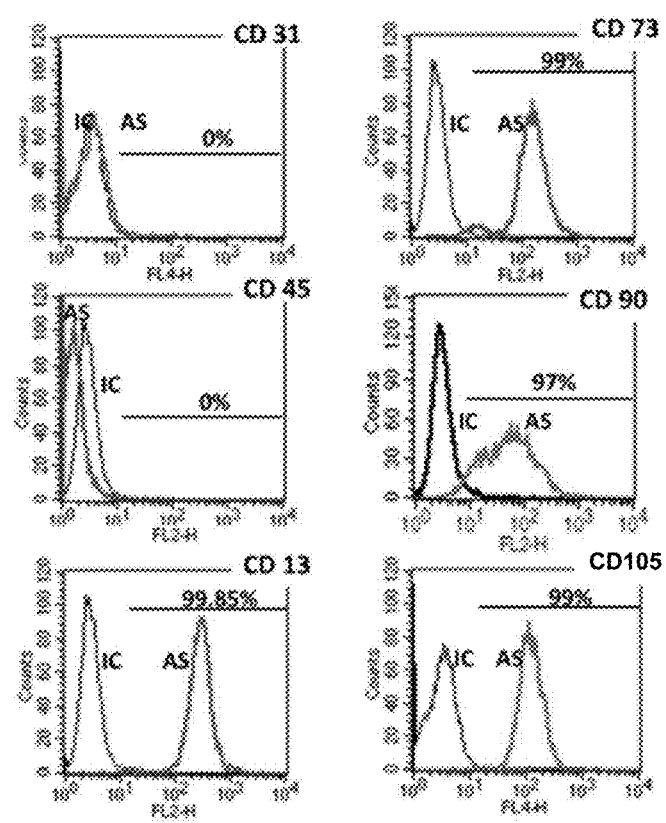

FIG. 39. Graph showing surface marker expression of hASC (IC-isotype controls and AS-antigen-specific antibodies).

DETAILED DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

As used herein, unless explicitly stated otherwise or clearly implied otherwise the term 'about' refers to a range of values plus or minus 10 percent, e.g. about 1.0 encompasses values from 0.9 to 1.1.

As used herein, unless explicitly stated otherwise or clearly implied otherwise the terms 'therapeutically effective dose,' 'therapeutically effective amounts,' and the like, refers to a portion of a compound that has a net positive effect on the health and wellbeing of a human or other animal. Therapeutic effects may include an improvement in longevity, quality of life and the like these effects also may also include a reduced susceptibility to developing disease or deteriorating health or wellbeing. The effects may be immediate realized after a single dose and/or treatment or they may be cumulative realized after a series of doses and/or treatments.

U.S. application Ser. No. 13/265,263, filed Oct. 19, 2011, discloses Materials and Methods for Using Adipose Stem Cells to Treat Lung Injury and Disease, and is itself a § 371 U.S. National Stage Entry of PCT/US2010/031808, filed Apr. 20, 2010, which claims priority to U.S. Provisional Application Ser. No. 61/170,910, filed Apr. 20, 2009, all of which are incorporated herein by reference in their entirety, as if each were incorporated by reference individually.

Surface marker expression of mASC was determined by flow cytometry. The majority of mASCs expressed the surface antigen of mesenchymal stem cells Sca-1, and were negative for the hematopoietic stem cell marker (CD45) and endothelial marker (CD31) (Data not shown).

Surface marker expression of hASC was determined by flow cytometry. The majority of hASC expressed stromal markers CD13, CD73, and CD105 and were negative for CD31 and CD45 (Data not shown).

Pharmaceutically acceptable salts include salts of compounds of the present disclosure that are safe and effective for use in mammals and that possess a desired therapeutic activity. Pharmaceutically acceptable salts include salts of acidic or basic groups present in compounds of the the present disclosure. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the disclosure may form pharmaceutically acceptable salts with various amino acids. Suitable base salts include, but are not limited to, aluminum, calcium, lithium, magnesium, potassium, sodium, zinc, and diethanolamine salts. For additional information on some pharmaceutically acceptable salts that can be used to practice the different embodiments described herein please, reviews such as Berge, et al., 66 J. PHARM. SCI. 1-19 (1977), Haynes, et al, J. Pharma. Sci., Vol. 94, No. 10, October 2005, pgs. 2111-2120 and the like.

Pilot studies exploring the effects of stem cells on lung injury in rodents and explanted human lungs were done with bone-marrow derived mesenchymal stem cells (MSC). These studies showed that MSC were able to suppress lung injury in LPS—(7-9), E. coli—(10), cecal ligation/puncture—(11, 12), and bleomycin-induced (13) lung injury models. In the past three years, reports show an increased interest in the application of another type of MSC, adipose-derived ASC, as a therapy for ARDS. This interest stems from the fact that ASC can be isolated in the therapeutic amounts immediately after the fat tissue harvest and enzymatic digestion, unlike MSC which will require weeks of propagation to arrive to the same cell yield (14). Therefore, ASC seem to be the cells of choice if autologous therapy is preferred, for example, in the hospital setting where access to the banked cells is limited. Thus far, ASC have been shown to suppress ARDS indices in the LPS—(15-18), cecal ligation/puncture—(19), ventilation—(20) and ischemia-reperfusion-induced (21) lung injury models.

Unlike relatively rare reports, demonstrating significant stem cell engraftment (9-16%) (22) and stem cell trans-differentiation into pulmonary cells (23), majority of reports focus on stem cell-mediated down-regulation of the acute inflammatory response and up-regulation of the pathways relevant to phagocytosis and bacterial clearance (7-11, 13). Discussed is a possibility that secreted soluble factors are sufficient to mediate promotion of an anti-inflammatory cytokine milieu in host. Lately, another possible mechanism of action, namely mitochondrial transfer from stem cell to host cell, was discovered (24). Whether or not secreted soluble factors are sufficient to exert therapeutic effects, or the presence of live stem cells is required for effective therapy, remains an open question.

Another important question is what cell delivery route would provide the most optimal therapeutic solution. Methods of cell delivery in preclinical studies of ARDS varied significantly and included intravenous (IV) (13, 15, 21, 22), intra-tracheal (IT) or oropharyngeal (OA) (8, 17, 18, 25), and intra-peritoneal (IP) (7, 19) administration. Whereas all methods yielded significant suppression of lung injury, the question of which route is the most feasible in the clinical setting remains. Although IT administration to anesthetized rodent was shown to render substantial cell delivery to the lung alveoli and decent cell retention for at least 24 h (18, 24), the issue of the efficient cell delivery to the distal airways of a ventilated patient urges researcher to think of alternative routes. Lung seems to be a privileged organ when it comes to the retention of IV-delivered particles (26, 27), as it represents the first capillary bed met by the particles delivered to the vein of the big circle of blood circulation. Not surprisingly, the first clinical trials of MSC (NCT01775774 at clinicaltrials.gov) and ASC (28) on ARDS utilize IV delivery of stem cells. However, one possible caveat of IV delivery is the thromboembolism of the lung (29); therefore the dosage and the speed of delivery, along with the vasoconstrictive status of the patient should be taken into account.

In the current study, the effects of ASC and their conditioned media on the lung injury in the murine model of LPS-induced ARDS were studied. The first objective of our study was to determine whether conditioned media of ASC (ASC-CM) can limit ARDS similar to ASC, and whether these two therapeutic agents suppress the same pathologic mechanisms of ARDS. The second objective was to compare the ability of naive and LPS-primed lung (and other organs) to retain IV-delivered ASC. This helped us ascertain how advantageous is intravenous cell delivery for the therapy of ARDS, and understand the dynamics of ASC retention in lung for future therapy optimization.

Materials and Methods

Materials. *E. coli* LPS 0127:B8 with the lot activity of 3,000,000 u/mg, FITC-dextran 40 kDa and carboxy-dichlorofluorescein diacetate (carboxy-DCFH-DA) were purchased from Sigma (St. Louis, Mo.). The antibody recognizing VE-cadherin were from Cayman. All reagents used for immunofluorescent staining were obtained from Invitrogen (Carlsbad, Calif.). All reagents for Flow Cytometry were from BD Biosciences.

Animals. C57Bl/6 mice were purchased from Harlan (Indianapolis, Ind.). Tie2CreERT2 mice were generously provided by Dr. Carlesso from Indiana University. Original founders (30) have been bred to C57BL/6 for 2 generations, then the strain has been maintained by brother×sister mating. All animal procedures were approved by Indiana University Institutional Animal Care and Use Committee and conformed to the requirements of Animal Welfare Act.

Cell Culture. HPAEC and NHDF were purchased from Lonza (Walkerville, Md.) and used at passages 5-8. Human ASC (hASC) were isolated from human subcutaneous adipose tissue samples obtained from liposuction procedures as previously described (31). Murine ASC (mASC), including ASC from heterozygous Tie2CreERT2 carriers, were isolated from subcutaneous fat from the hip area using similar procedure. Briefly, fat was excised from the anesthetized animal, minced and digested with 2 mg/ml collagenase type 1 (Worthington) at 37° C. Digests were centrifuged at 300 g to separate floating adipocytes. Pellet containing stromal vascular fraction was re-suspended in EBM2 (Lonza) with 5% FBS, filtered through 100μ nylon filter, and centrifuged again at 300 g. Cells were re-suspended in EGM2-MV (Lonza), let adhere to plastic, and propagated in EGM2-MV until 3 d passage at 37° C. in a humidified atmosphere of 5% $CO_2$-95% air. Before injection, cells were trypsinized and re-suspended in EBM2 at concentration of $3\times10^6$ cell/ml.

Flow Cytometry. mASC passage 3 were harvested, cell numbers were determined using hemocytometer, and cell suspensions were incubated for 20 min on ice with fluorophor labeled anti-Sca-1 (mouse ASC marker), anti-CD31 (EC markers) and anti-CD45 (hematopoietic marker) IgG (BD). Human ASC were tested for CD13, CD73, CD 105 (positive selection markers), CD106 (negative in ASC as opposed to MSC), CD31, and CD45 markers. Corresponding IgG were used as isotype control. Flow cytometry was performed using a Calibur flow cytometer and Cell QuestPro software (BD).

Generation of Conditioned Media. Conditioned media for the assessment of effects on endothelial permeability was generated from ASC and NHDF using EGM2MV as basis media. 50-60% confluent ASC or NHDF were incubated with EGM2MV $0.2$ ml/cm$^2$. Media was collected 24 h later, and kept frozen until future analysis. Conditioned media for mouse experiments was generated from 60-70% confluent mASC using EBM2 with 0.5% C57Bl/6 mouse serum (Innovative Research, Novi, Mich.), concentrated 10 times with 3 kDa cut-off filter (Amicon), and kept frozen until injection into animal.

Assessment of ARDS Indices. 2 mg/kg LPS or equal volume of saline was delivered by oropharyngeal aspiration to isoflurane-anesthetized 20-25 g C57Bl/6 mouse as described in (18). In pilot experiment, animal temperature was assessed with rectal probe every 2 h. In ASC/ASC-CM experiment, 300 000 murine ASC (passage 3) or 0.2 ml of concentrated ASC-CM were injected into tail vein 4 h after LPS administration. 24-48 h later, animals were sacrificed for analysis. For the assessment of vascular leak and lung inflammation, Evans Blue Dye (EBD)-albumin conjugate (0.5% EBD in 4% BSA solution) was administered in the tail vein (30 mg/kg) 1 h prior experiment termination. In anesthetized animal, the chest cavity was opened; blood was sampled by cardiac puncture to determine level of circulating EBD. Lungs were washed from blood by injecting saline via the right ventricle. Bronchoalveolar lavage fluid (BALF) was obtained by flushing lung with 3 ml of ice-cold PBS. Lungs were excised, homogenized in formamide to extract EBD (18 h, 60° C.); optical density was determined at 620 and 750 nm. Extravasated EBD concentration was calculated using a standard curve and normalized to circulating EBD level. BALF was centrifuged at 600 g to sediment cells; supernatant was snap-frozen for future ELISA and protein analyses. Pellet was subjected to red cells lysis; remaining cells were separated by cytospin and stained with Diff Quick staining kit. Cells were identified under Nikon microscope 40× objective; total of 300 cells was counted on each slide. For immunohistochemistry, lungs were perfused with warm 4% formaldehyde/agarose solution, embedded in paraffin, sectioned and analyzed with Nikon microscope (10× magnification objective).

Cell Tracing Experiment. LPS stimulation of C57Bl/6 mice was done as described above. ASC derived from Tie2CreERT2 mice (30) (passage 3) were re-suspended at $3\times10^6$ cell/ml in the EBM2 containing FITC-dextran, and injected into tail vein (300 000 cells per mouse) 4 h after LPS administration. To ascertain the efficiency of cell injection, 10 min after injection blood was sampled from the saphenous vein and analyzed for FITC fluorescence. Animals anesthetized with isoflurane were exsanguinated; lung, heart, spleen, kidney, brain and liver were collected immediately after cell injection, or 2 h, 24 h, 48 h later. Organs were snap-frozen in liquid nitrogen. Minced organs were subjected to complete digestion with enzymes from mini kit Tissue IBI ( ), and genomic DNA free of mRNA was extracted. Primers gDNA was analyzed with quantitative Real-Time RT-PCR (qRT-PCR) for the presence of CRE transgene, using D19mit1 as a loading control. To establish that there is no tissue-specific interference with RT-PCR reaction, calibration curves were created for gDNA from each organ of interest isolated directly from Tie2CreERT2 animal. Amount of CRE+ cells per organ was calculated knowing that the mouse cell contains 5.6 pg per cell, and using the difference in C, to calculate the difference in the content of CRE+ gDNA between the organ from Tie2CreERT2 heterozygous animal and the organ from the C57Bl/6 mouse injected with cells from Tie2CreERT2 heterozygous animal.

Assessment of ROS Generation. The method for the measurement of oxidative activation of neutrophils was based on the ROS-dependent oxidation of carboxy-DCFH-DA to carboxy-DCF (32). Polymorphonuclear leukocytes (PMN) from BALF of LPS- and LPS/ASC-CM treated mice were pipetted to the wells of 96-well plate (60,000 cells per well), pre-loaded with 12.5 µg/ml carboxy-DCFH-DA, and then stimulated with 1 µg/ml LPS for 20 h. Wells with no cells containing same concentration of dye were used as controls. Fluorescence was read in the FITC channel of fluorometer/plate reader.

Measurement of Transendothelial Permeability. Permeability of HPAEC monolayers for FITC-dextran was measured using 0.4µ polyester trans-well inserts (Costar) as described in (33). Briefly, HPAEC were plated on collagenized inserts, whereas ASC or NHDF were plated on the bottom of wells. HPAEC were allowed to reach confluence. Alternatively, HPAEC were pretreated with un-concentrated ASC or NHDF conditioned media mixed with EGM2MV (1:1) for 72 h. Media were changed to basal media 1 h prior the beginning of the experiment. FITC-dextran was added to the top chamber to the final concentration 1.75 mg/ml; immediately after, monolayers were stimulated with 0.25 mM $H_2O_2$; media was sampled from the bottom chamber 2 h after and analyzed for FITC-dextran fluorescence.

Transendothelial electrical resistance (TER) was measured using the highly sensitive biophysical assay with an electrical cell-substrate impedance sensor (ECIS) (Applied Biophysics, Troy, N.Y.) as described previously (33). HPAEC were plated on gold microelectrodes in EGM2MV; then exposed to the un-concentrated conditioned media/EGM2MV mixture (1:1) for 72 h. At the end of pre-incubation period, resistance of monolayers reached 1000-1200 Ohm, evident of monolayer confluence. Media were changed to basal media 1 h prior the beginning of the experiment.

HPAEC Imaging. For immunofluorescence experiments, HPAEC monolayers were plated on gelatin-covered coverslips and grown to confluence. Cells were exposed to the un-concentrated conditioned media mixed with EGM2MV (1:1) for 72 h; media were changed to basal media 1 h prior the beginning of the experiment. After stimulation, cells were fixed, permeabilized and stained with VE-cadherin-specific antibodies and Alexa594-conjugated phalloidin. Coverslips were viewed and photographed using Nikon fluorescent microscope (40× objective).

Statistical Analysis. Quantitative data are presented as mean±SEM. Statistical analysis was performed by t-test using Origin 8.0. A probability value of $\leq 0.05$ was considered statistically significant.

Flow Cytometric Analyses of Adipose-Derived Mesenchymal Stem Cell Surface Markers. Both murine and human ASC used in our study were originally produced by the propagation of cell fraction adherent to plastic under standard culture condition. mASC and hASC appeared to be of a regular size, spindle shape, and fibroblastic morphology in culture, which is consistent with mesenchymal stromal cells. Referring now to FIG. 38, analysis of mASC at passage 3 revealed that these cells are negative for endothelial marker CD31 and marker of hematopoietic origin CD45. mASC were positive for Sca-1, mesenchymal cell marker of murine origin (34). Referring now to FIG. 39, analysis of hASC at passage 3 demonstrated negligible staining for CD31 and CD45 markers and positive staining for the stromal markers CD13, CD73, and CD 105. Consistent with the data of literature, CD106 staining was weaker than what would be expected in the bone-derived MSC (35).

Figure 1A:
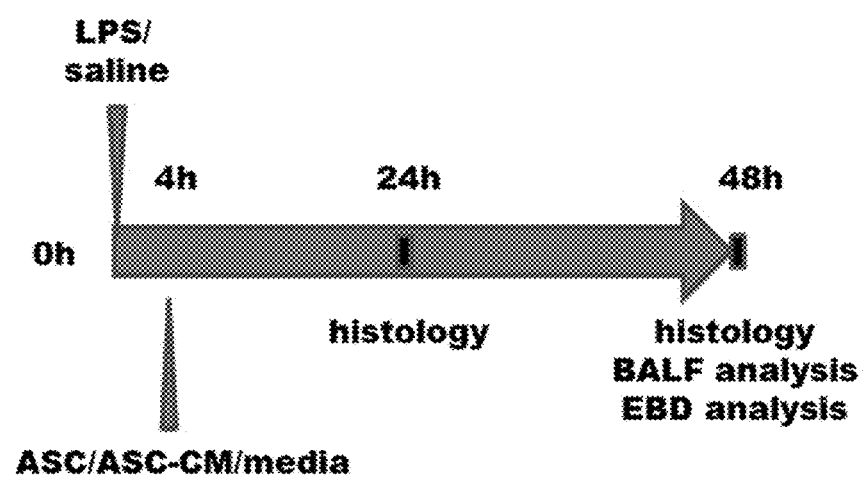
FIG. 1A. Diagram showing timeline of the in vivo study design.
Figure 1B:
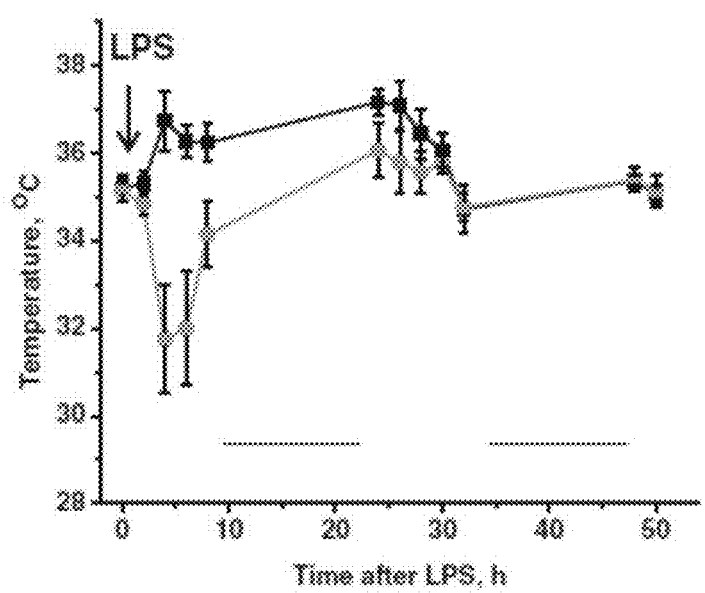
FIG. 1B. Graph illustrating body temperatures of mice after administering saline (black) or LPS (grey) via oropharyngeal aspiration (N=4 per group).
Figure 1C:
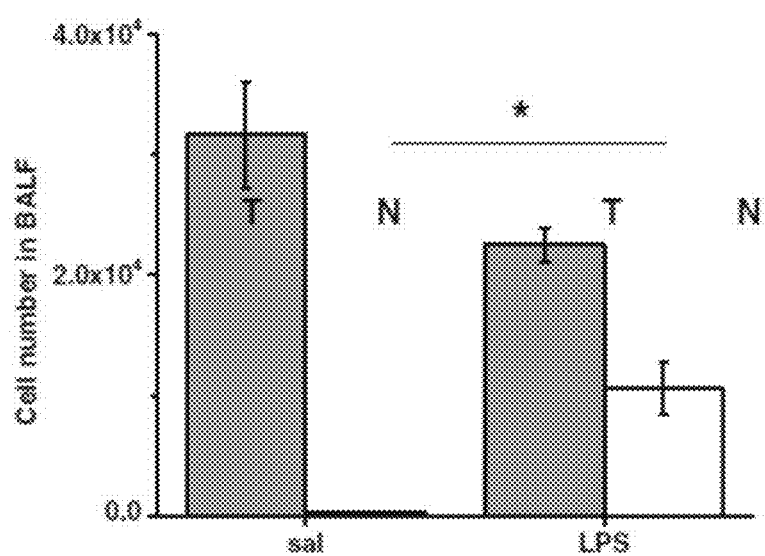
FIG. 1C. Bar graph showing the total cell number of WBC (T, dark grey) and neutrophil (N, white) in BALF of mice after administering saline or LPS (N=3 per group).

Study Design. Referring now to FIG. 1A, the study design for the assessment of the ASC and ASC-CM effects on LPS-induced lung injury is shown. LPS or saline were delivered into lungs through the oropharyngeal aspiration. Intravenous ASC, ASC-CM or control media injections were performed 4 h after LPS delivery. The scheme was designed to ascertain that the therapeutic intervention occurs when the first clinical signs of ARDS development become evident. To provide some reference points applicable for comparison with patients' status, the animal temperature and assessed neutrophil infiltration in BALF were monitored. Referring now to FIG. 1B, the mice experience hypothermic response peaking at 4-6 h following LPS administration. The first time point of the day was 8 a.m. Referring now to FIG. 1C, the total cell number of White Blood Cell (WBC) and neutrophil in BALF were measured after administering saline or LPS. Although total WBC count does not change significantly 4 h post-LPS administration, the presence of neutrophil in BALF is already apparent at this time point. Therefore, this model allows us to study limitation of an ongoing ARDS in mice.

Figure 2A:
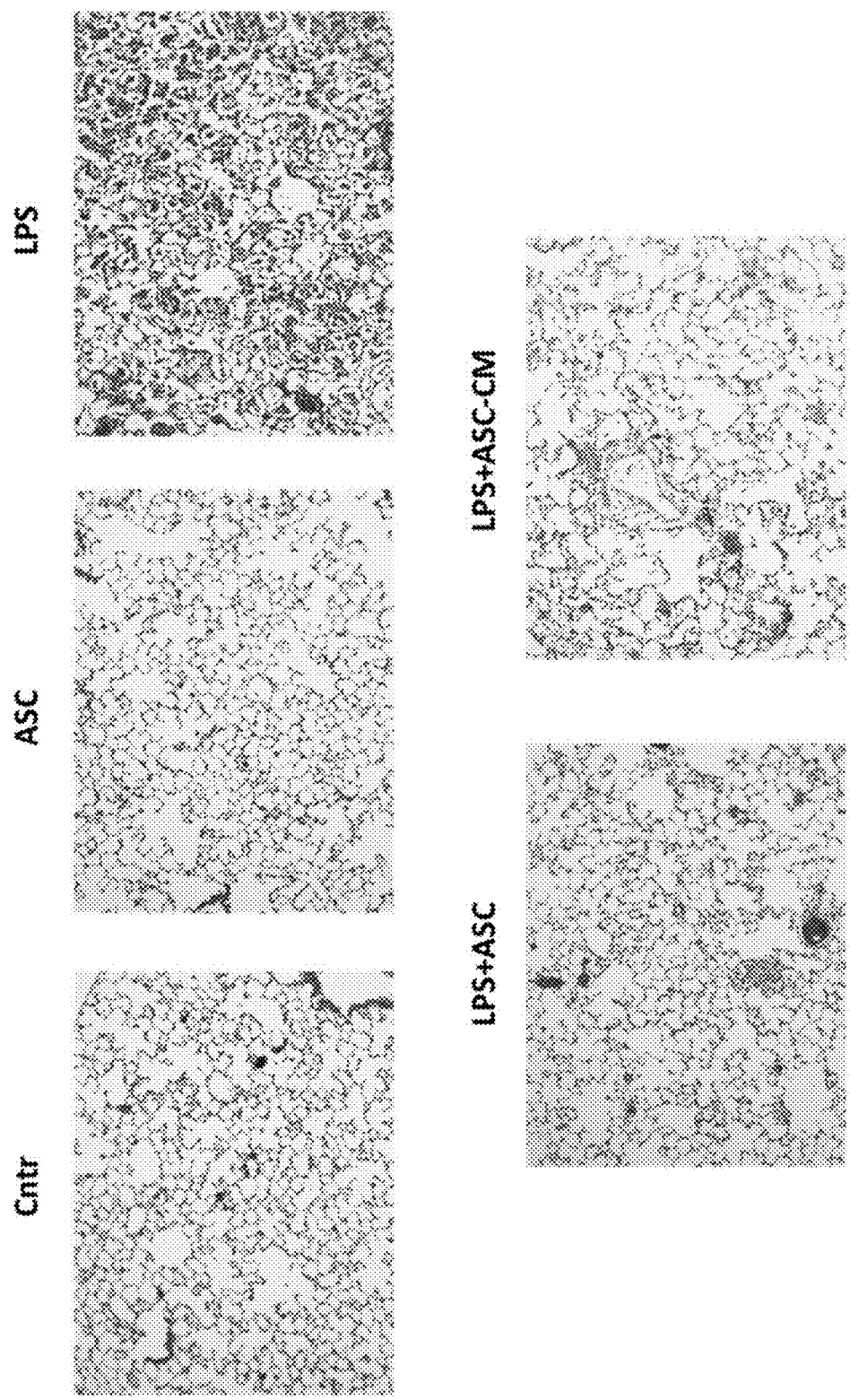
FIG. 2A. Photographs of murine alveolar stained with hematoxylin/eosin harvested from lungs treated with saline (Cntr), ASC, LPS, LPS+ASC, or LPS+ASC-CM. Histopathology of lung 48 h post-saline/LPS is shown at 10× magnification (660×830μ)
Figure 2B:
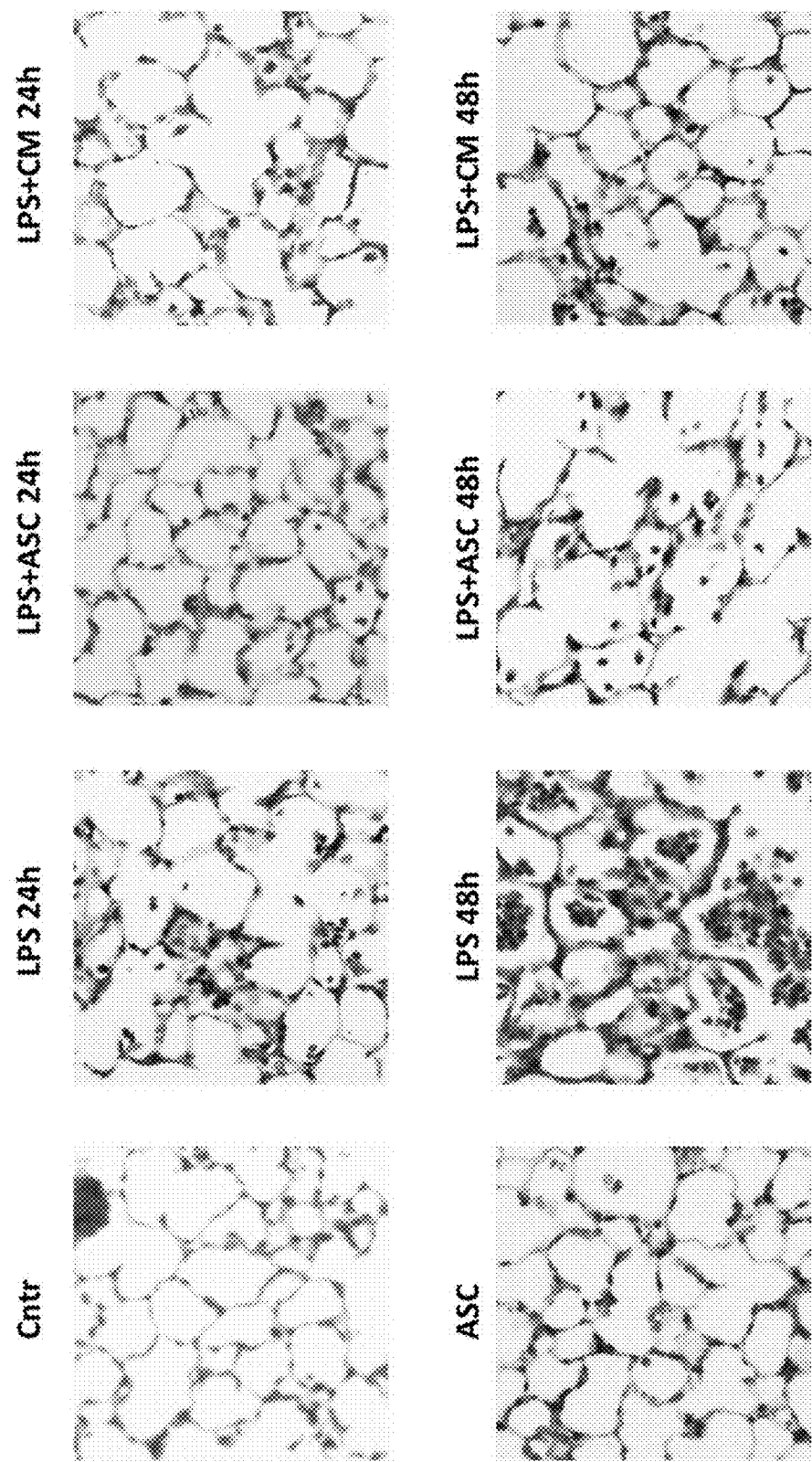
FIG. 2B. Photographs of murine alveolar stained with hematoxylin/eosin harvested from lungs treated with saline (Cntr), ASC, LPS, LPS+ASC, or LPS+ASC-CM. The high power fields (150×150μ) are shown for the time points indicated.

Histopathologic Findings of the Lung. Referring now to FIGS. 2A and 2B, hematoxylin and eosin staining of the lung sections revealed no apparent signs of inflammatory response in saline-treated lungs of mice who received ASC or control media injection. LPS triggered lung inflammation, which was evident at 24 h and progressed to more severe stage at 48 h. In mice receiving control media injection, LPS caused marked infiltration of neutrophils and red blood cells into interstitial spaces and airspaces, as well as swelling of the alveolar walls. In contrast, systemic delivery of ASC or ASC-CM significantly suppressed accumulation of cells and debris in the alveolar sacs and reduced septum thickening.

Figure 3A:
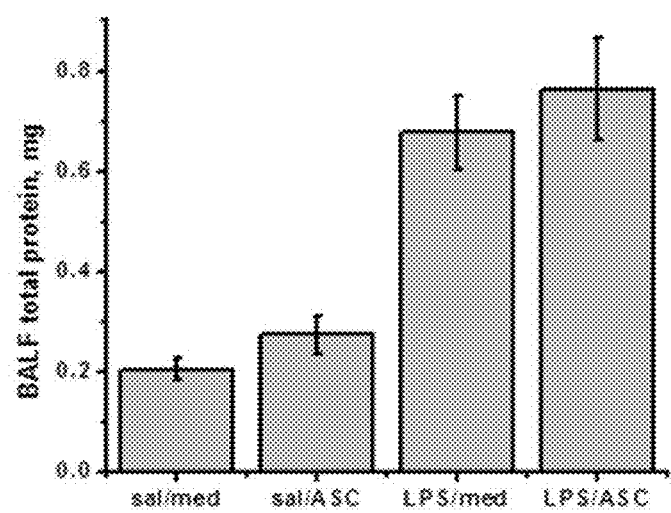
FIG. 3A. Bar graph showing the total protein level in BALF treated with saline (sal/med), saline+ASC, LPS (LPS/med), or LPS+ASC.
Figure 3B:
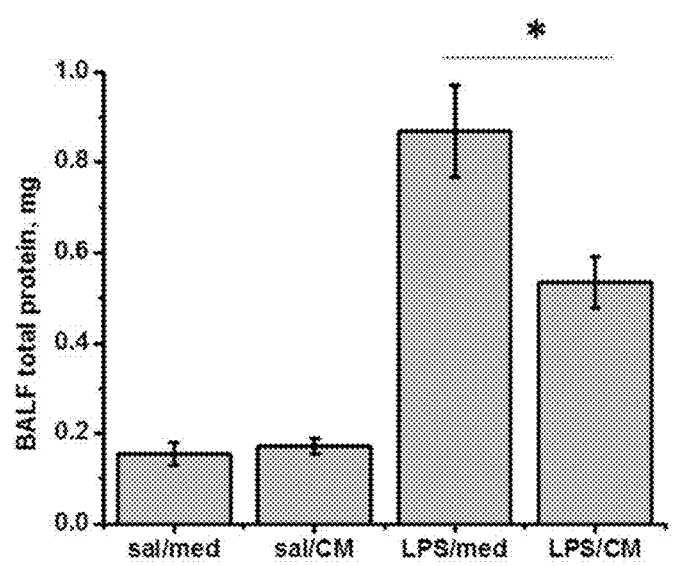
FIG. 3B. Bar graph showing the total protein levels in BALF treated with saline (sal/med), saline+ASC-CM, LPS (LPS/med), or LPS+ASC-CM.
Figure 3C:
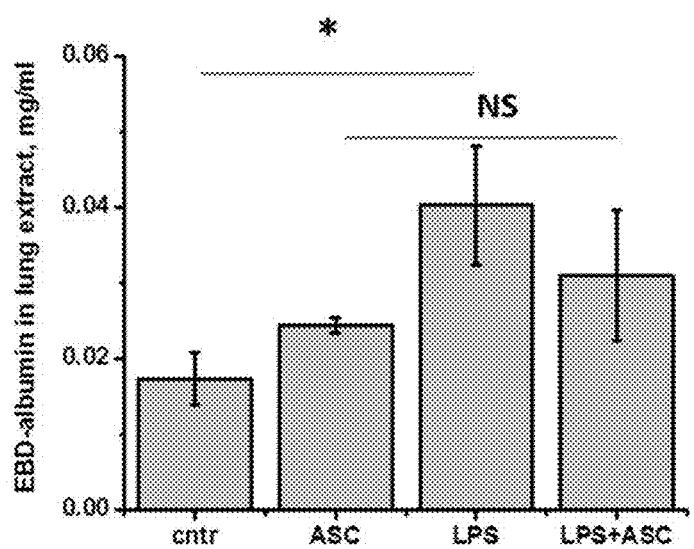
FIG. 3C. Bar graph showing the level of EBD extravasation in BALF treated with saline (cntr), ASC, LPS, or LPS+ASC.

ASC and ASC-CM Effects on Lung Permeability and Neutrophil Infiltration. Referring now to FIGS. 3A and 3B, assessment of total protein content in BALF showed the significant increase of protein level in response to LPS administration. ASC-CM treatment markedly suppressed this LPS-induced protein increase 44 h post-injection, whereas ASC treatment had no effect. On the contrary, ASC was able to suppress LPS-induced increase in EBD extravasation (FIG. 3C), whereas ASC-CM effect was not significant (data not shown).

Figure 4A:
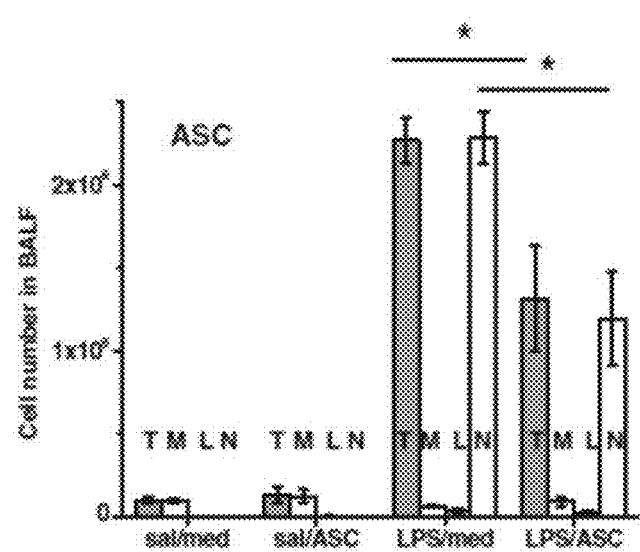
FIG. 4A. Bar graph showing the cell number of WBC (T), macrophage (M), lymphocytes (L), neutrophil (N) in BALF treated with saline (sal/med), saline+ASC, LPS (LPS/med), or LPS+ASC.
Figure 4B:
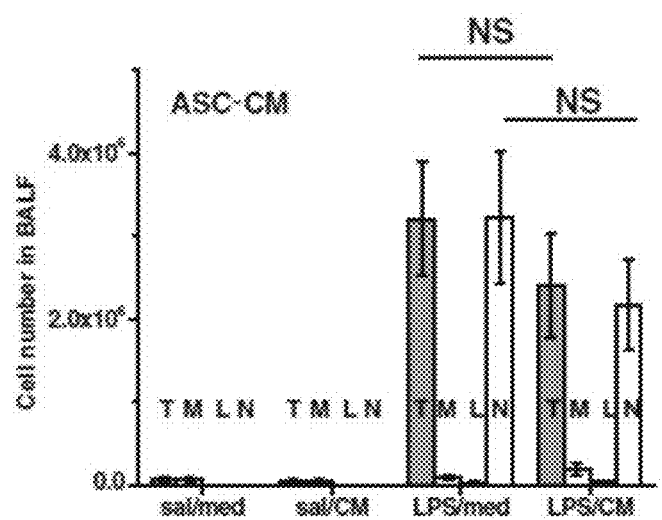
FIG. 4B. Bar graph showing the cell number of WBC (T), macrophage (M), lymphocytes (L), neutrophil (N) in BALF treated with saline (sal/med), saline+ASC-CM, LPS (LPS/med), or LPS+ASC-CM.
Figure 4C:
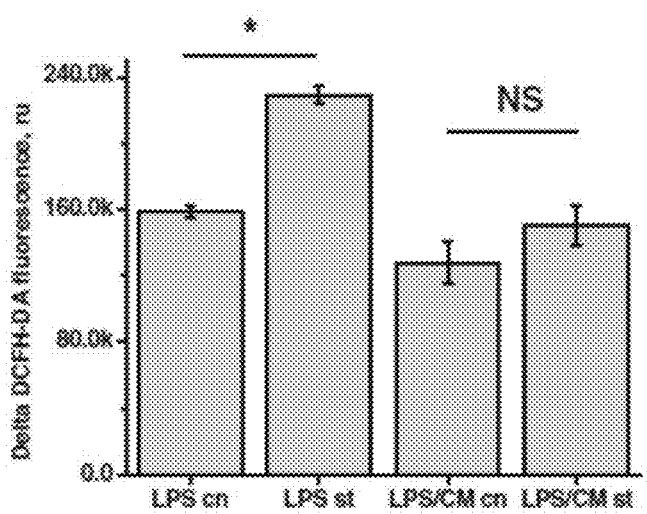
FIG. 4C. Bar graph illustrating the effect on LPS-induced ROS generation by WBC. WBC from BALF of LPS-challenged mice were subjected to vehicle (LPS cn) or 1 g/ml LPS stimulation (LPS st). In parallel, WBC from BALF of LPS/ASC-CM-treated mice were subjected to vehicle (LPS/CM cn) or LPS/CM stimulation (LPS/CM st).

Referring now to FIGS. 4A and 4B, assessment of total WBC count in BALF showed that the number of cells in airspaces increased dramatically in response to LPS stimulation. Whereas residential lung macrophages comprised the majority of cells in BALF from saline lungs, neutrophils were the dominant cell type in BALF from LPS lungs. Total WBC (grey) and PMN (light grey) counts in BALF were significantly reduced by mASC. The balance between macrophages, lymphocytes and neutrophils in BALF of LPS-treated mice was not significantly affected by either therapeutic agent. Referring now to FIG. 4C, WBC from BALF of LPS-challenged mice were subjected to vehicle (LPS cn) or 1 µg/ml LPS stimulation (LPS st). In parallel, WBC from BALF of LPS/ASC-CM-treated mice were subjected to vehicle (LPS/CM cn) or LPS/CM stimulation (LPS/CM st). LPS-induced ROS generation by WBC from BALF of LPS/ASC-CM mice was significantly lower comparing to WBC from BALF of LPS/media mice. Although ASC or ASC-CM treatment did not shift the neutrophil/macrophage balance noticeably (FIG. 4C), the significant suppression of total WBC count was evident in LPS mice receiving ASC injection. Similar trend in ASC-CM receiving mice was observed, but did not reach significance at 44 h post-injection. To further characterize possible mechanisms of ASC-CM-mediated lung injury limitation, the ability of BALF WBC from LPS- and LPS/ASC-CM-receiving mice to generate ROS were measured. WBC from mice receiving LPS were induced by LPS stimulation, whereas WBC from LPS/ASC-CM receiving mice no longer respond to LPS stimulation.

Figure 5A:
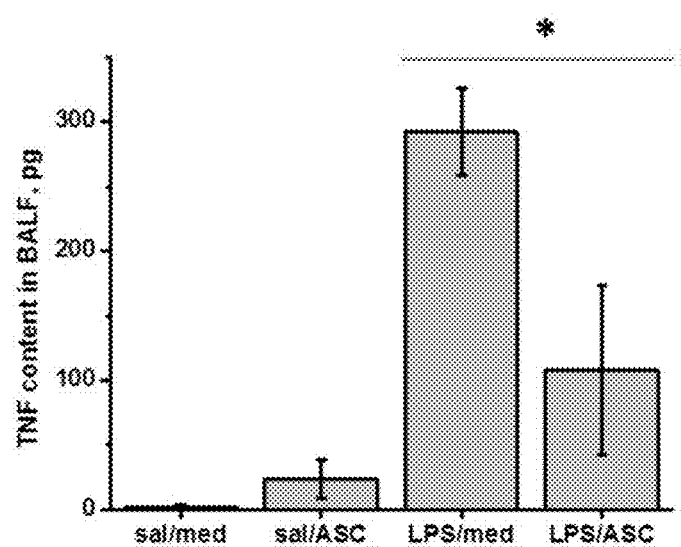
FIG. 5A. Bar graph showing the level of pro-inflammatory cytokine TNFα in BALF treated with saline (sal/med), saline+ASC, LPS (LPS/med), or LPS+ASC.
Figure 5B:
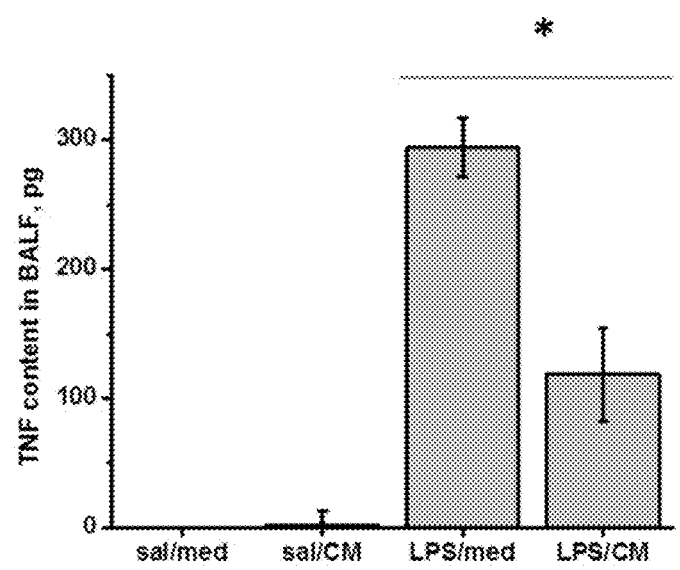
FIG. 5B. Bar graph showing the level of pro-inflammatory cytokine TNFα in BALF treated with saline (sal/med), saline+ASC+CM, LPS (LPS/med), or LPS+ASC+CM.
Figure 5C:
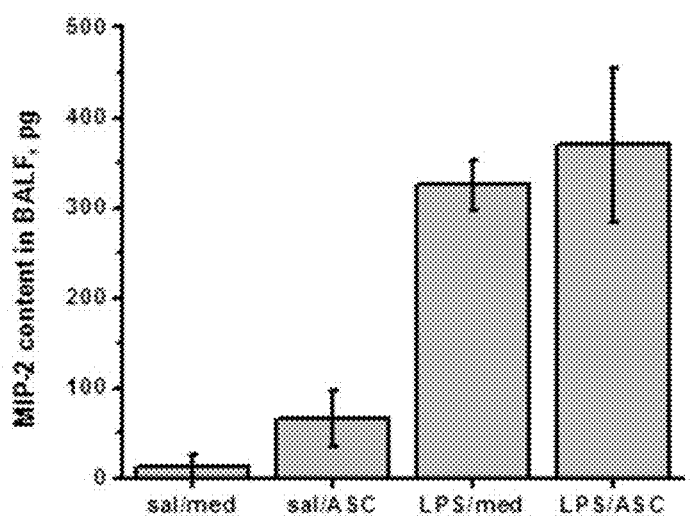
FIG. 5C. Bar graph showing the level of pro-inflammatory cytokine MIP-2 in BALF treated with saline (sal/med), saline+ASC, LPS (LPS/med), or LPS+ASC.
Figure 5D:
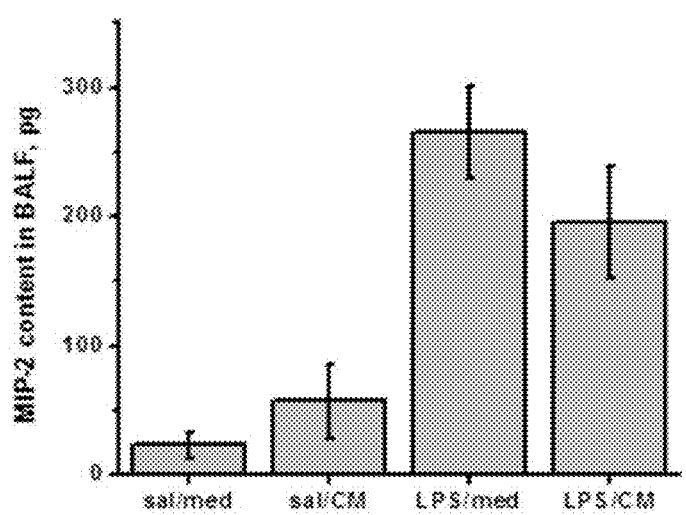
FIG. 5D. Bar graph showing the level of pro-inflammatory cytokine MIP-2 in BALF treated with saline (sal/med), saline+ASC+CM, LPS (LPS/med), or LPS+ASC+CM.
Figure 6A:
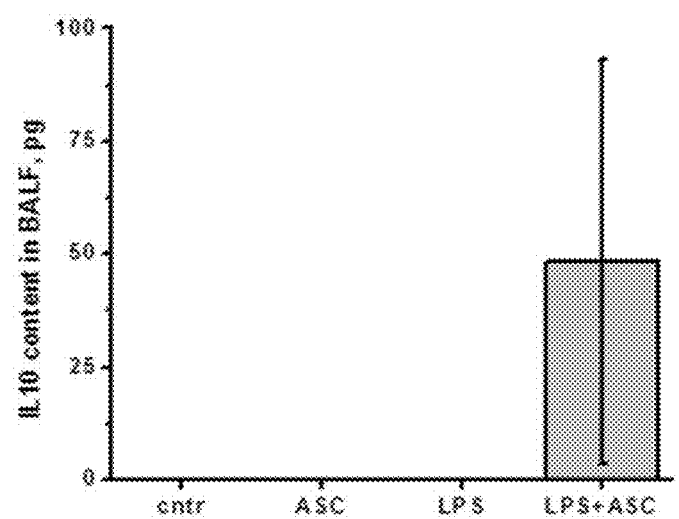
FIG. 6A. Bar graph showing the level of anti-inflammatory IL-10 in BALF treated with saline (sal/med), saline+ASC, LPS (LPS/med), or LPS+ASC.
Figure 6B:
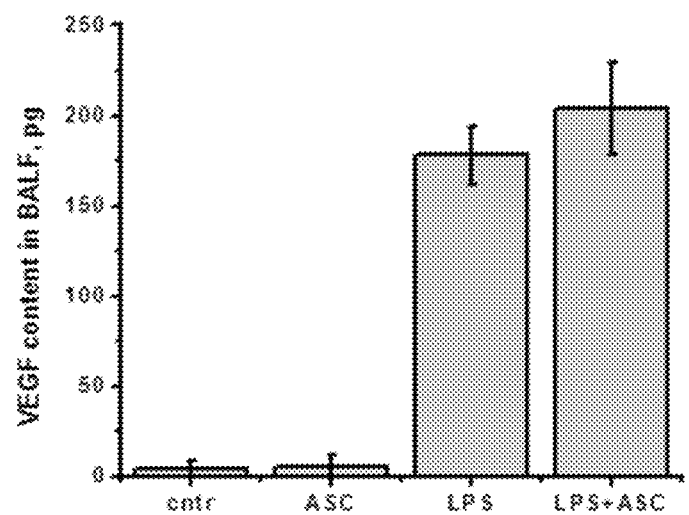
FIG. 6B. Bar graph showing the level of pro-angiogenic factor VEGF in BALF treated with saline (sal/med), saline+ASC, LPS (LPS/med), or LPS+ASC.
Figure 6C:
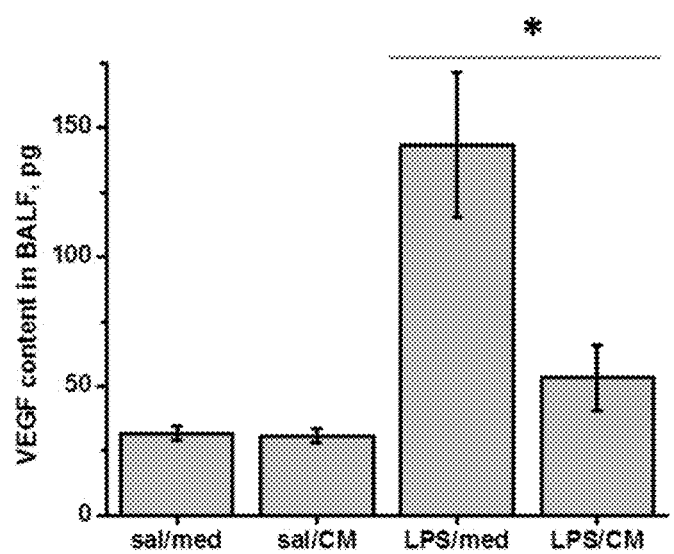
FIG. 6C. Bar graph showing the level of pro-angiogenic factor VEGF in BALF treated with saline (sal/med), saline+ASC-CM, LPS (LPS/med), or LPS+ASC-CM.

ASC and ASC-CM Effects on Pro-Inflammatory and Anti-Inflammatory Cytokines and Pro-Angiogenic Factors. To determine the effect of ASC and ASC-CM on inflammation progression/resolution, the level pro-inflammatory TNFα, MIP-2 and anti-inflammatory IL-10 in lung were measured. Referring now to FIG. 5A to 5D, LPS caused marked increase in the level of TNFα and MIP 2. After 44 hours of ASC injection or conditioned media (ASC-CM) injection, LPS-induced increase in TNFα level was suppressed by both therapeutic agents (FIGS. 5A and 5B), whereas increase in MIP2 level was not affected significantly (FIGS. 5C and 5D). Referring now to FIG. 6A, the level of anti-inflammatory IL-10 remained below detection in control mice or mice challenged with LPS. Increase in BALF IL-10 content was observed in response to ASC, but not ASC-CM (data not shown). Referring now to FIGS. 6B and 6C, LPS-induced level of VEGF in BALF was non-significantly increased in ASC-treated mice, but markedly suppressed in ASC-CM-treated mice.

Figure 7A:
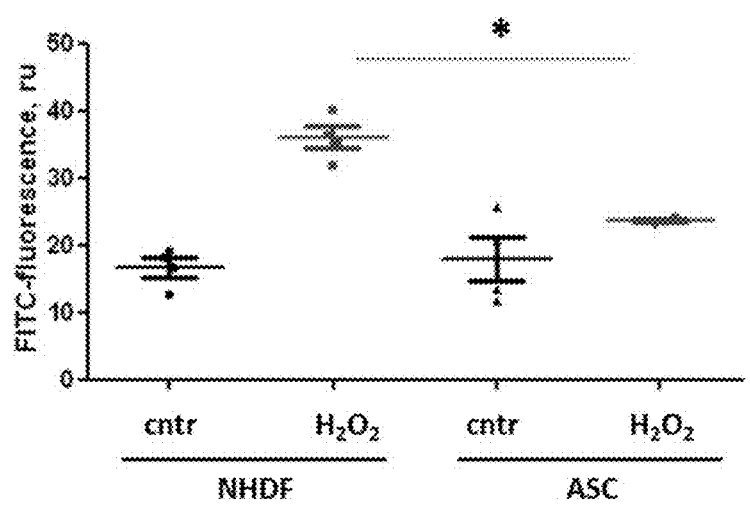
FIG. 7A. Graph of results from transendothelial permeability assay conducted in vitro on a monolayer of human pulmonary artery endothelial cells (HPAEC). These results are from HPAECs exposed to the following conditions: a control (cntr+NHDF); $H_2O_2$+NHDF; cntr+ASC; and $H_2O_2$+ASC.
Figure 7B:
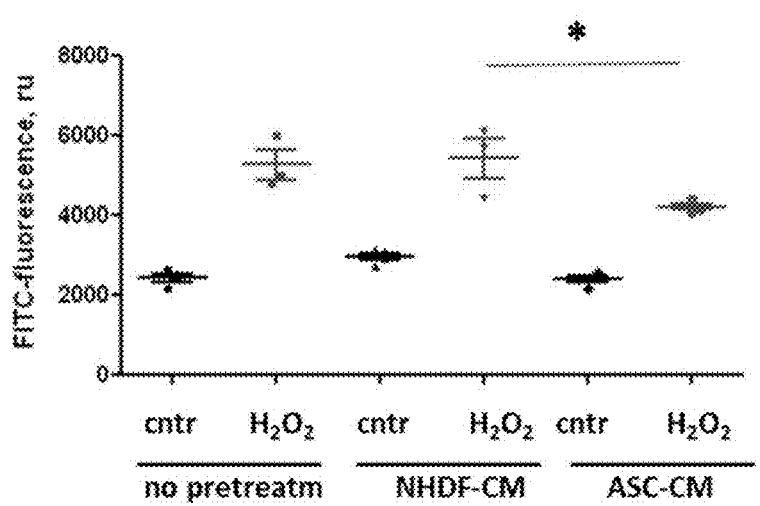
FIG. 7B. Graph of results from transendothelial permeability assay conducted in vitro on a monolayer of HPAEC. These results are from HPAECs exposed to the following conditions: control with no pretreatment (cntr); $H_2O_2$; control with pretreatment (cntr+NHDF); $H_2O_2$+NHDF; cntr+ASC-CM; and $H_2O_2$+ASC-CM.
Figure 7C:
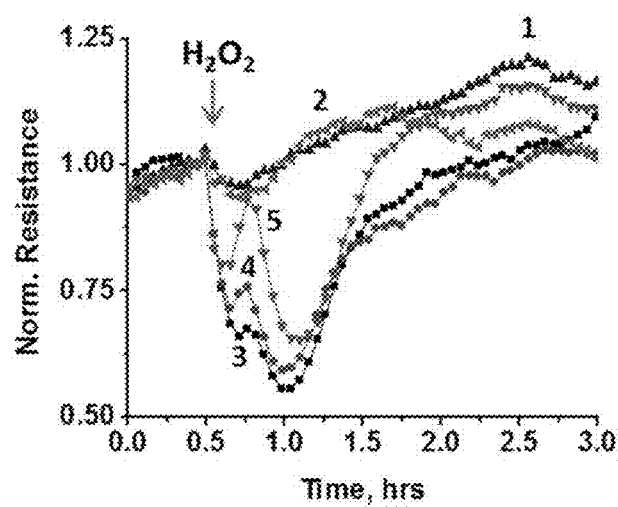
FIG. 7C. Graph illustrating results from transendothelial electrical resistance (TER) conducted in vitro on a monolayer of HAPEC. HAPECs were grown on gold electrodes of ECIS arrays in the presence of NHDF-CM or ASC-CM. Shown are the means of 3 parallel recordings for each pretreatment/stimulation: 1) blue—unstimulated HPAEC pretreated with NHDF-CM; 2) purple—unstimulated HPAEC pretreated with ASC-CM; 3) black—stimulated with $H_2O_2$ HPAEC which were not pretreated with CM; 4) red—stimulated with $H_2O_2$ HPAEC pretreated with NHDF-CM; 5) teal—stimulated with $H_2O_2$ HPAEC pretreated with ASC-CM.
Figure 8:
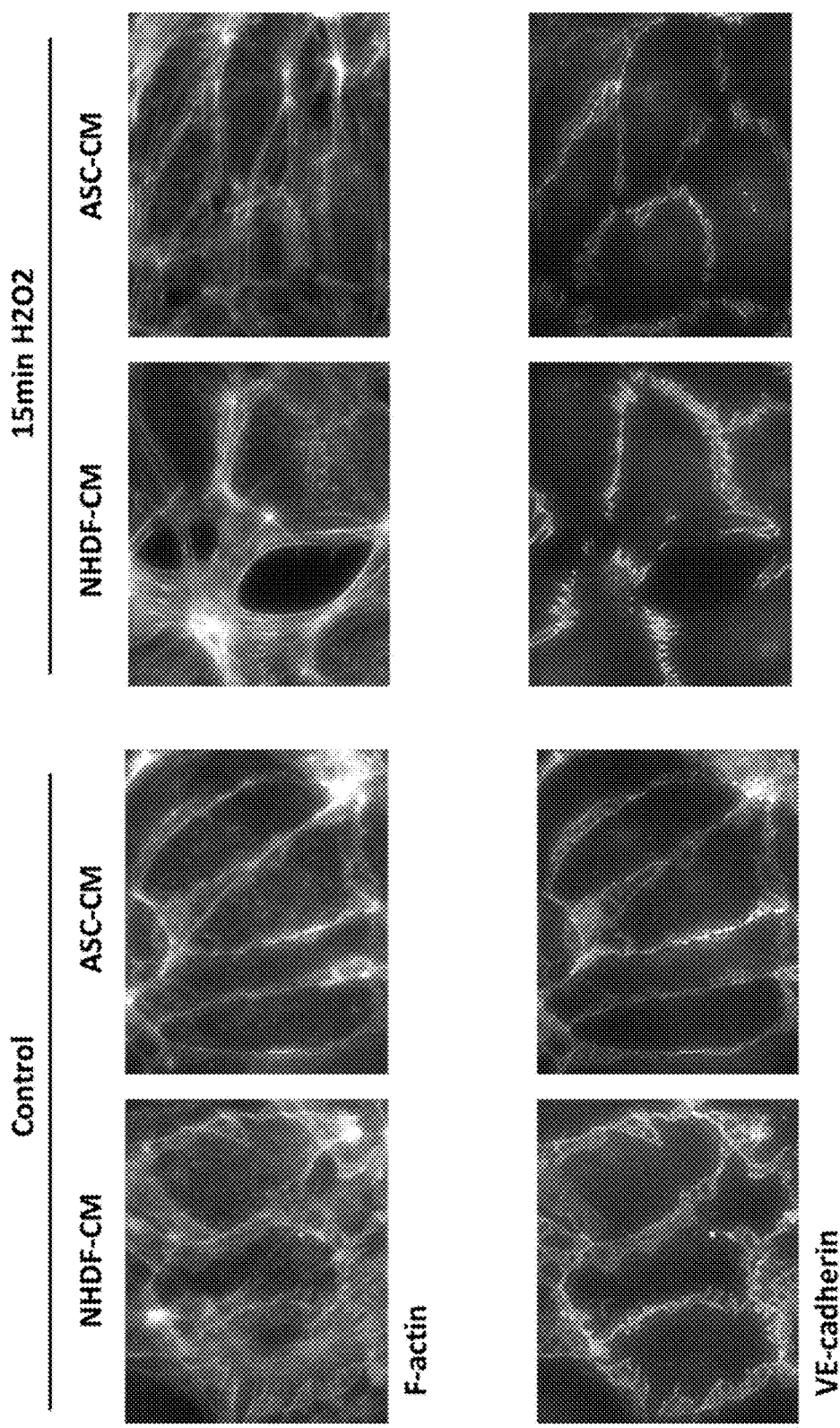
FIG. 8. Photographs of HPAEC monolayers stained with F-actin and VE-cadherin. The results are from HPAECs exposed to the following conditions: a control (cntr+NHDF); $H_2O_2$+NHDF; cntr+ASC; and $H_2O_2$+ASC.

ASC and ASC-CM Effects on Endothelial Permeability In Vitro. To further analyze mechanisms underlying ASC and ASC-CM effects on lung permeability, ASC/ASC-CM effects on endothelial monolayer barrier function were assessed directly. First, HPAEC monolayers were grown on collagenized polyester inserts in the presence of ASC/NHDF in the lower chamber. Prior to analysis, inserts were transferred to the fresh wells to avoid the possibility of direct ROS scavenging by ASC/NHDF. Top chamber was loaded with FITC-dextran, and monolayers were stimulated with edemagenic product of the neutrophil oxidative burst 250 μM $H_2O_2$. Referring now to FIG. 7A, a marked HPAEC barrier dysfunction observed in response to $H_2O_2$ was significantly attenuated by the treatment of ASC. Referring now to FIG. 7B, similar to HPAEC grown in the presence of ASC, HPAEC grown in the presence of ASC-CM responded to $H_2O_2$ with less barrier dysfunction. To further characterize ASC-CM-mediated stabilization of HPAEC barrier, transendothelial electrical resistance (TER) was measured. HPAEC grown on gold electrodes were pretreated with ASC-CM or NHDF-CM; then stimulated with $H_2O_2$. Control monolayers responded to $H_2O_2$ with marked reduction of TER, which was restored within 3 h period. Referring now to FIG. 7C, NHDF-CM-pretreated monolayers displayed similar response curve, whereas TER reduction in ASC-CM-pretreated monolayers was significantly attenuated. Referring now to FIG. 8, immunofluorescent analysis of NHDF-CM-pretreated HPAEC showed that $H_2O_2$ caused marked rearrangement of actin cytoskeleton along with the distortion of junctional organization and gap formation in endothelial monolayers. ASC-CM-pretreated HPAEC displayed less severe changes in response to $H_2O_2$ with attenuated gap formation.

Retention of IV-Delivered ASC in Lungs and Other Organs. To ascertain whether IV delivery of stem cell material facilitates the therapy of ARDS, the distribution of ASC in different organs of naïve and LPS-challenged mice were analyzed. The ASC from genetically modified mouse, namely CRE transgene carriers, which gave us an opportunity to detect cells by the genomic DNA analysis for the presence of CRE transgene were examined. Comparison of titration curves for CRE transgene with titration curves for D19mit1 marker (1 locus per genome) revealed the presence of ≥10 loci of CRE transgene in the genome of donor transgenic mouse, which significantly improved our ability to detect CRE+ cells in organs with limited CRE+ cell distribution. Analysis of lung from ASC-injected mice receiving saline showed that approximately 10% of injected dose was retained in lungs for at least 2 h following cell injection. This amount was markedly reduced in the next 24 h, coming down to the negligible level 48 h post-injection. On the contrary, LPS-challenged lung retained significantly less cells initially (less than 5% of injected dose); this level was increased within next 2 h, remained stable for the following 24 h, and was still substantial 48 h post-injection. As spleen was shown recently to participate in stem cell "processing", whether time-dependent decrease in CRE+ cell retention in lung correlates with an increase in CRE+ cell level in spleen were analyzed. It was found that spleen retained significantly less cells per mg of weight. Importantly, no increase in CRE+ cell content was noted between 24 h and 48 h, when control lung manifested CRE+ cell clearance. Analysis of liver, kidney, brain and heart also demonstrated minor cell retention comparing to lung. None of the organs harbored CRE+ cells deporting control lung in the period between 24 and 48 h. Interestingly, majority of analyzed organs show control/LPS cell ratio opposite to the one observed in lung 2 h post-injection. CRE+ cell content in spleen, liver, kidney and brain of mice challenged with LPS was higher than that content in organs of control mice. 48 h post-injection, the only organ still showing significant CRE+ cell retention was LPS-challenged lung.

Figure 9:
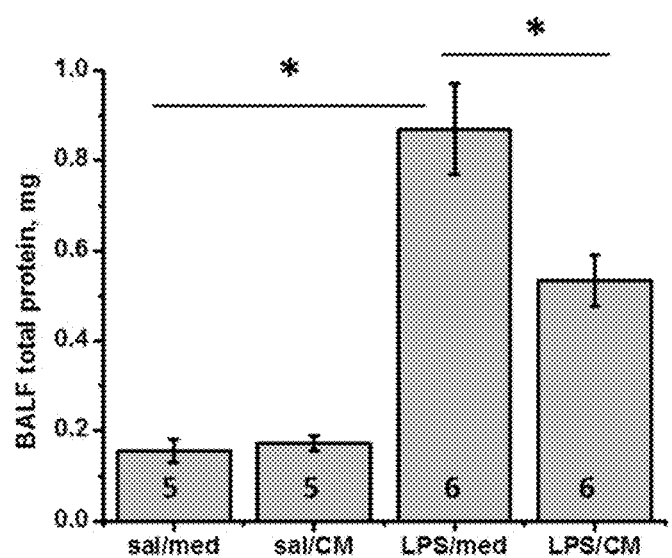
FIG. 9. Bar graph showing the total protein levels in BALF treated with saline (sal/med), saline+ASC-CM, LPS (LPS/med), or LPS+ASC-CM.
Figure 10:
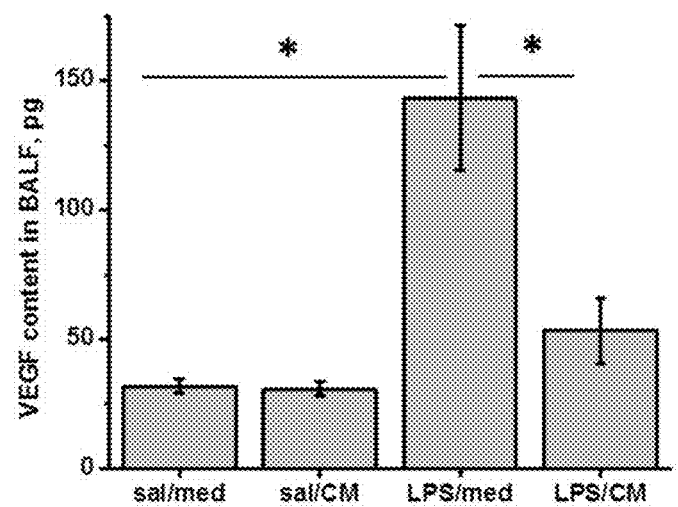
FIG. 10. Bar graph showing the level of pro-angiogenic factor VEGF in BALF treated with saline (sal/med), saline+ASC-CM, LPS (LPS/med), or LPS+ASC-CM.
Figure 11:
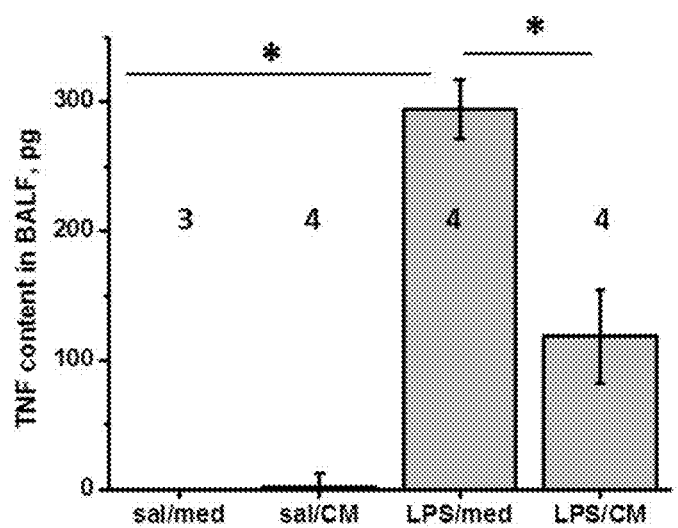
FIG. 11. Bar graph showing the level of pro-inflammatory cytokine TNFα in BALF treated with saline (sal/med), saline+ASC+CM, LPS (LPS/med), or LPS+ASC+CM.
Figure 12:
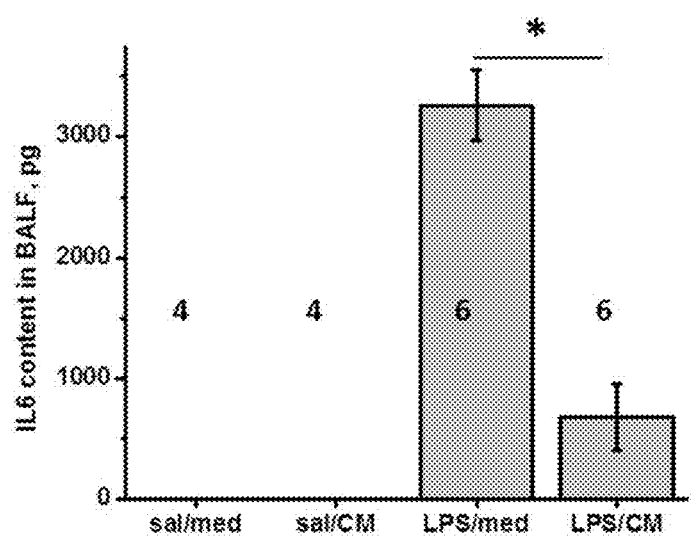
FIG. 12. Bar graph showing the level of IL-6 in BALF treated with saline (sal/med), saline+ASC+CM, LPS (LPS/med), or LPS+ASC+CM.

ASC-CM Effects on Permeability and Inflammation in LPS-Challenged Lungs. Referring now to FIG. 9, total protein level in BALF was increased in LPS-challenged mice. LPS-induced increase in total protein level was reduced in response to ASC-CM injection. Referring now to FIG. 10, VEGF level in BALF was increased in LPS-challenged mice. LPS-induced increase in VEGF level was reduced in response to ASC-CM injection. Referring now to FIG. 11, TNF-α level in BALF was increased in LPS-challenged mice. LPS-induced increase in TNF-α level was reduced in response to ASC-CM injection. Referring now to FIG. 12, IL-6 level in BALF was increased in LPS-challenged mice. LPS-induced increase in IL-6 level was reduced in response to ASC-CM injection.

Figure 13:
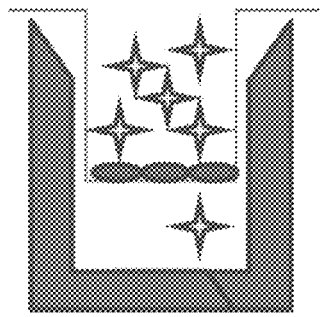
FIG. 13. Schematic diagram showing a type of transendothelial permeability assay using a polyester insert that has porous membrane. Fluorescent dye (star) was loaded on the top of a polyester insert, on which endothelial cells (circles) were grown. Increased fluorescence in the bottom of the chamber indicates the increase in permeability.
Figure 14:
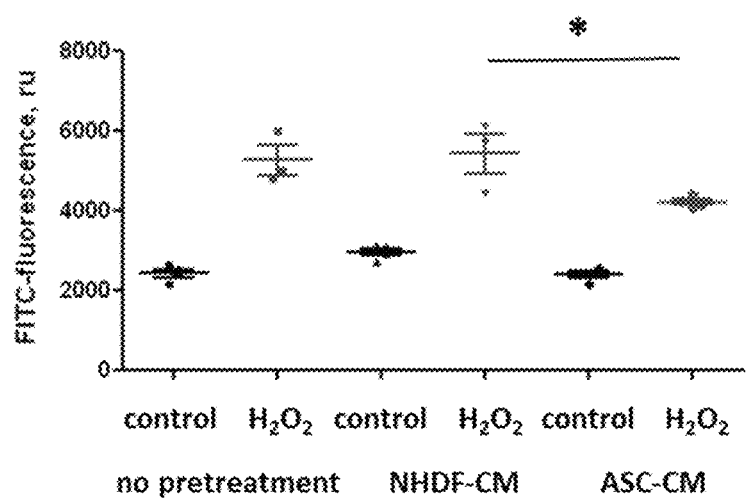
FIG. 14. Graph of results from transendothelial permeability assay conducted in vitro on a monolayer of HPAEC. These results are from HPAECs exposed to the following conditions: control with no pretreatment (cntr); $H_2O_2$; control with pretreatment (cntr+NHDF); $H_2O_2$+NHDF; cntr+ASC-CM; and $H_2O_2$+ASC-CM.
Figure 15:
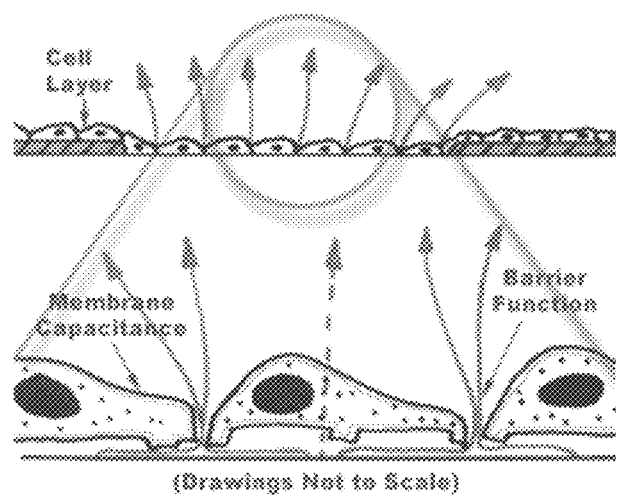
FIG. 15. Schematic diagram shows a type of transendothelial permeability assay using Electric Cell-substrate Impedance Sensor (ECIS).
Figure 16:
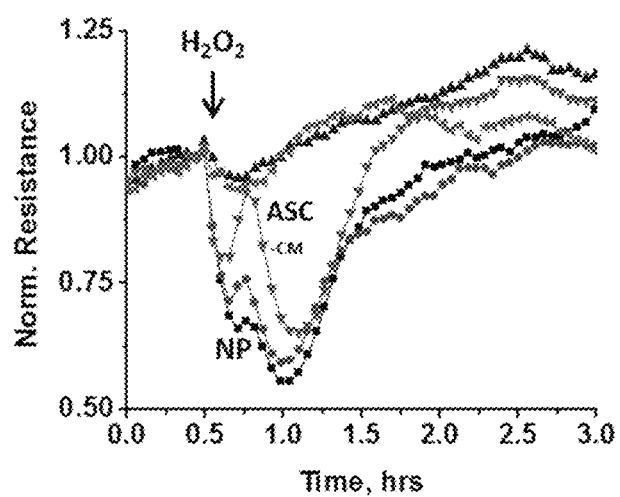
FIG. 16. Graph illustrating results from transendothelial electrical resistance (TER) conducted in vitro on a monolayer of endothelial cells. Endothelial cells were grown on gold electrodes of ECIS arrays in the presence of NHDF-CM or ASC-CM.
Figure 17:
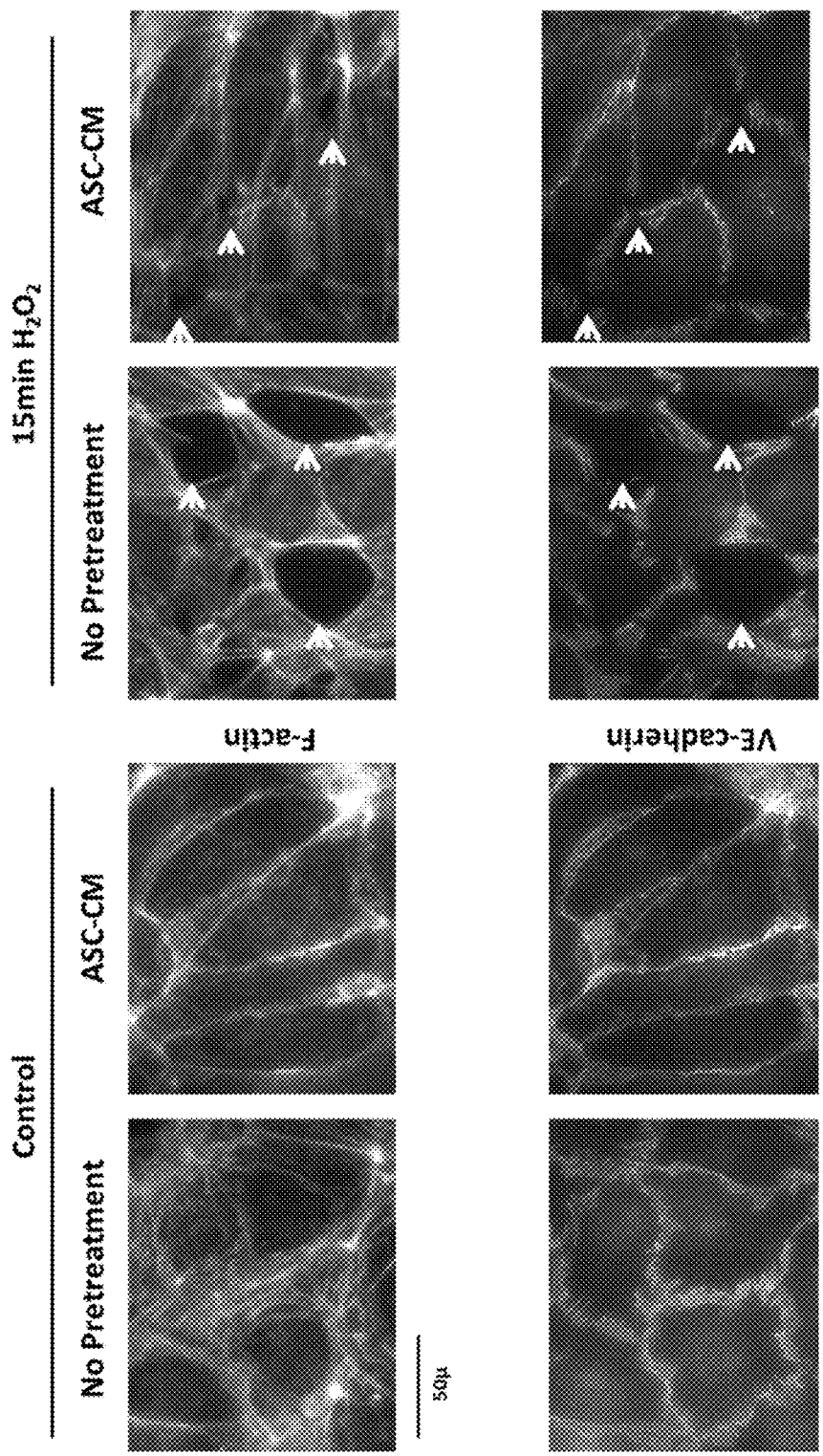
FIG. 17. Photographs of HPAEC monolayers stained with F-actin and VE-cadherin. The results are from HPAECs exposed to the following conditions: a control with no pretreatment; a control with pretreatment of ASC-CM; $H_2O_2$; and $H_2O_2$+ASC.
Figure 19:
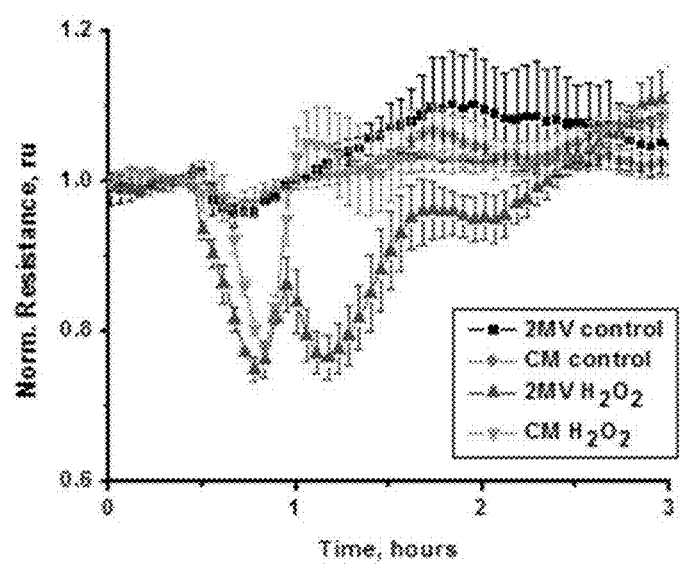
FIG. 19. Graph illustrating results from transendothelial electrical resistance (TER) conducted in vitro on a monolayer of endothelial cells. The figure shows the effect of ASC-CM on resistance without heat-inactivation.
Figure 20:
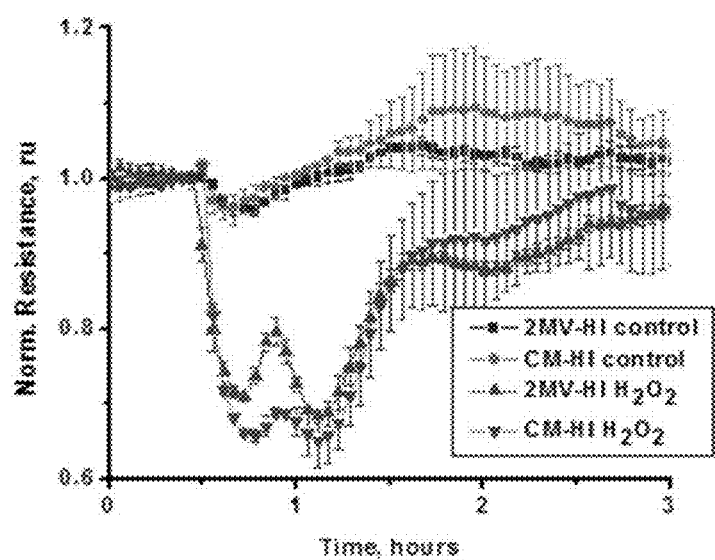
FIG. 20. Graph illustrating results from transendothelial electrical resistance (TER) conducted in vitro on a monolayer of endothelial cells. The figure shows the effect of ASC-CM on resistance with heat-inactivation.
Figure 22:
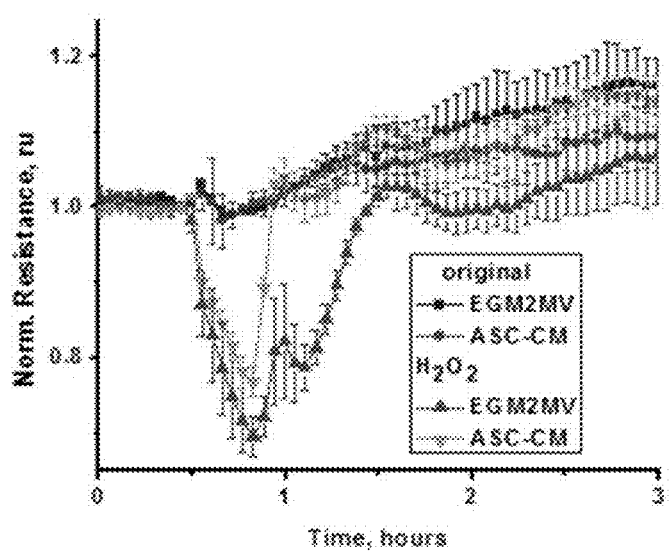
FIG. 22. Graph illustrating results from transendothelial electrical resistance (TER) conducted in vitro on a monolayer of endothelial cells. The figure shows the effect of ASC-CM on resistance after the depletion of exosomes via ultracentrifugation.
Figure 23:
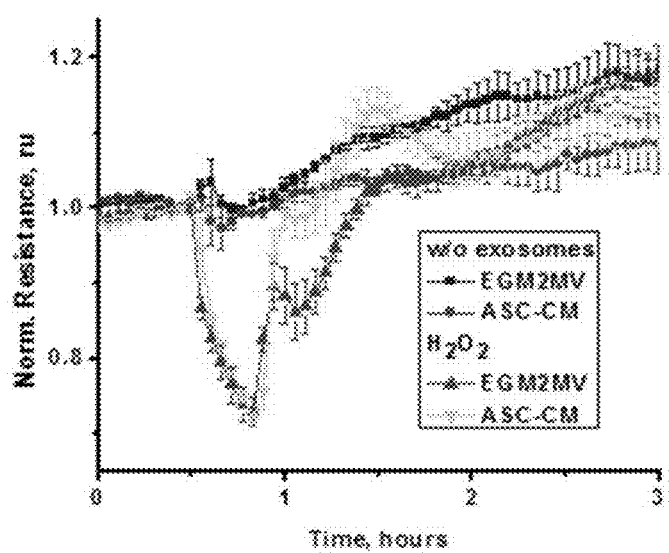
FIG. 23. Graph illustrating results from transendothelial electrical resistance (TER) conducted in vitro on a monolayer of endothelial cells. The figure shows the effect of ASC-CM on resistance after the depletion of exosomes via ultracentrifugation.
Figure 24:
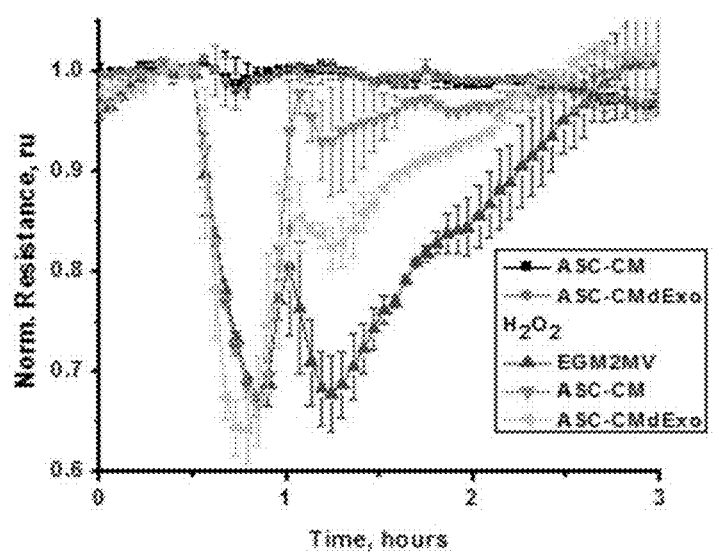
FIG. 24. Graph illustrating results from transendothelial electrical resistance (TER) conducted in vitro on a monolayer of endothelial cells. The figure shows the effect of ASC-CM on resistance after the depletion of exosomes via ultracentrifugation.
Figure 26:
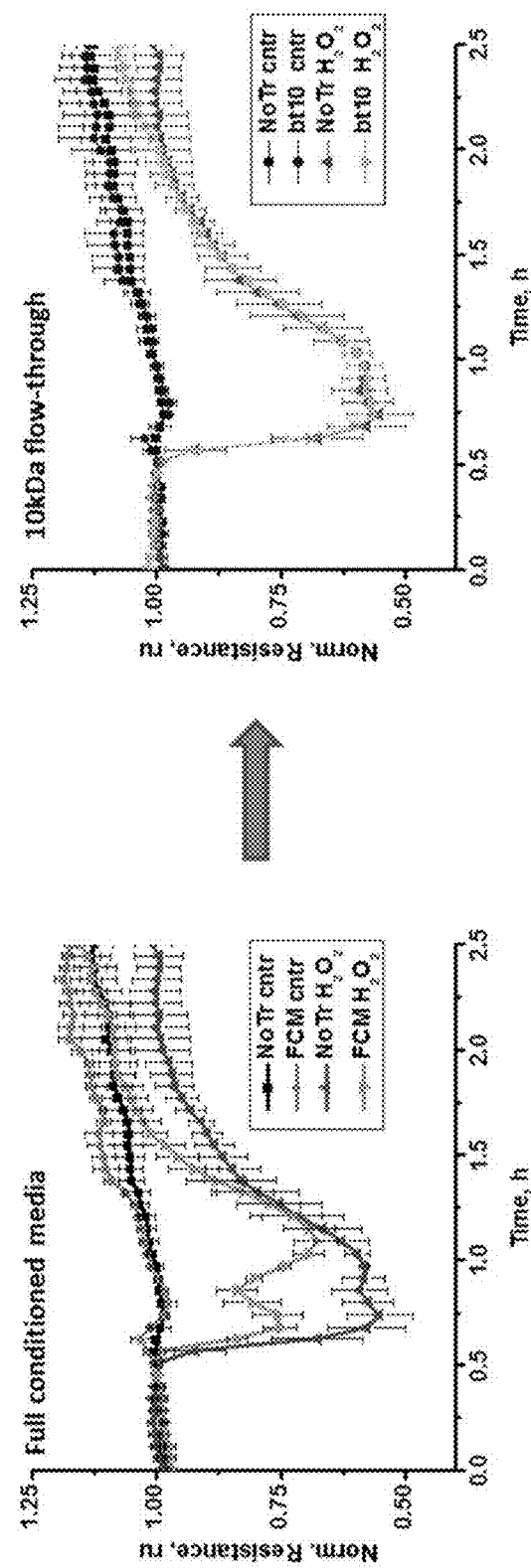
FIG. 26. Graph illustrating results from transendothelial electrical resistance (TER) conducted in vitro on a monolayer of endothelial cells. The figure shows the effect of ASC-CM flow-through on barrier function using a 10 kDa cut-off filter.
Figure 27:
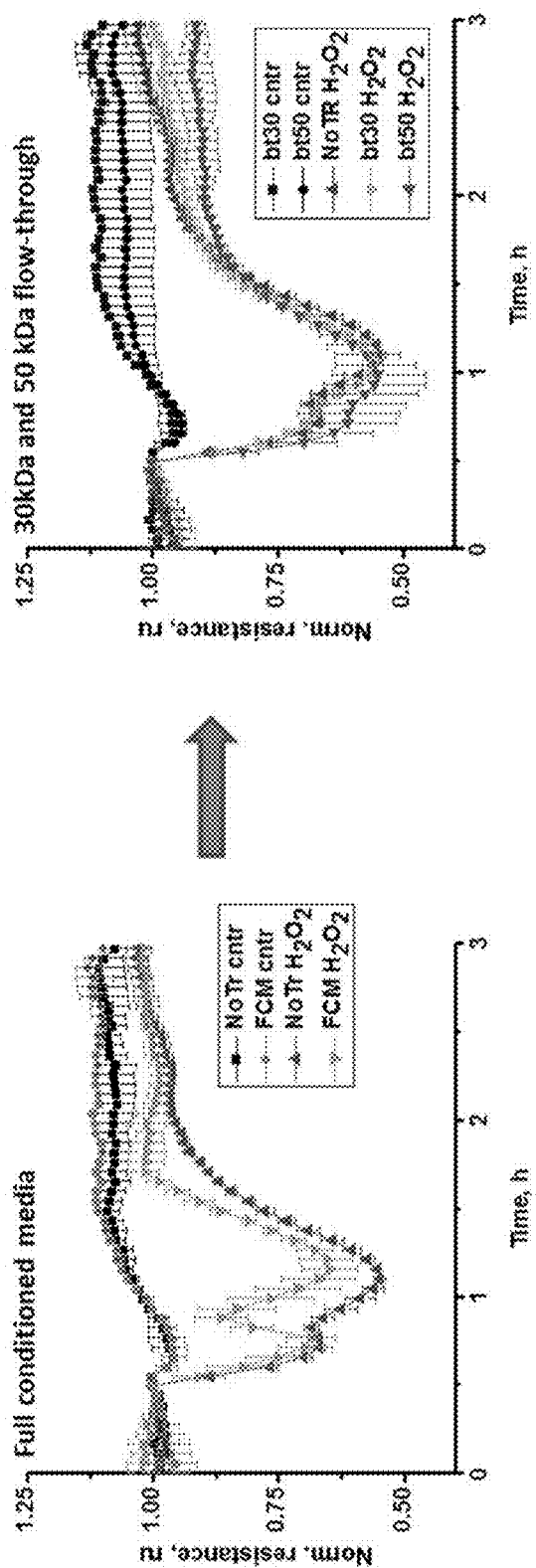
FIG. 27. Graph illustrating results from transendothelial electrical resistance (TER) conducted in vitro on a monolayer of endothelial cells. The figure shows the effect of ASC-CM flow-through on barrier function using 30 kDa and 50 kDa cut-off filters.
Figure 28:
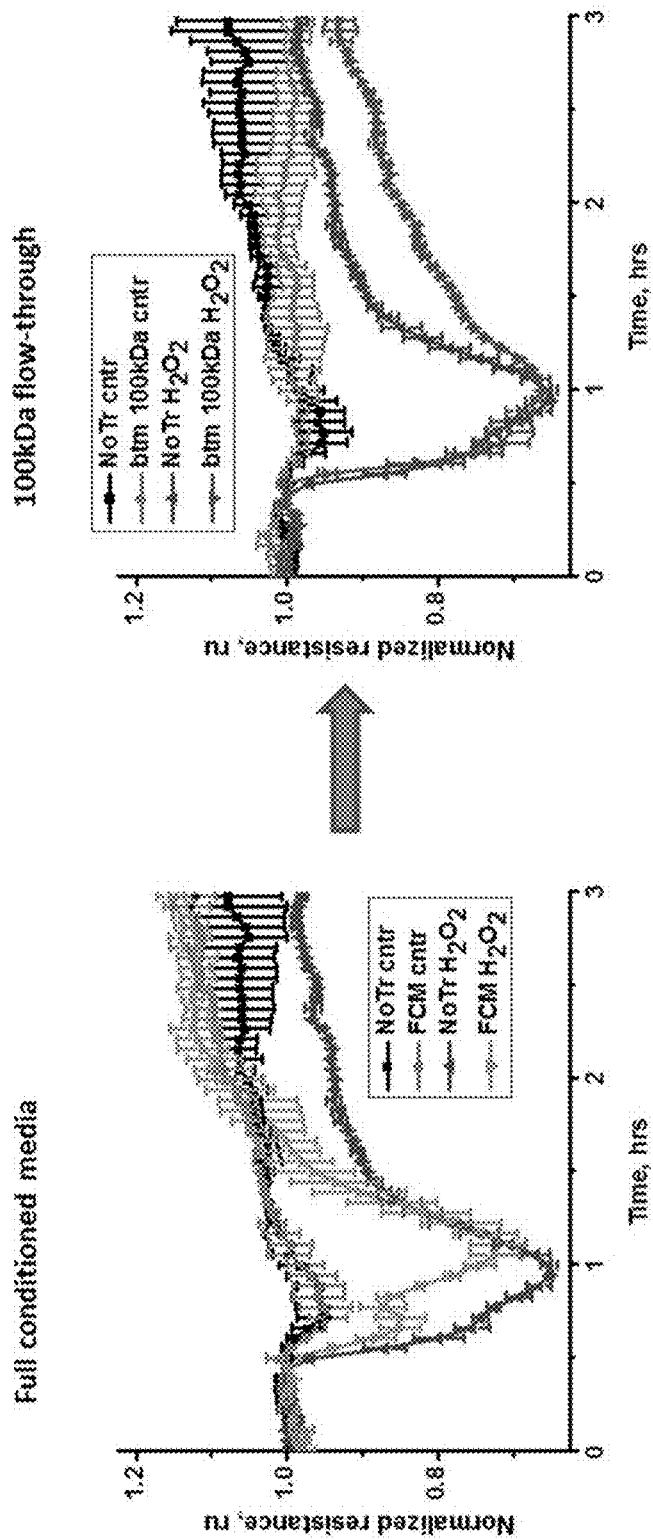
FIG. 28. Graph illustrating results from transendothelial electrical resistance (TER) conducted in vitro on a monolayer of endothelial cells. The figure shows the effect of ASC-CM flow-through on barrier function using a 100 kDa cut-off filter.

ASC-CM Effects on Endothelial Permeability In Vitro. Referring now to FIG. 13, endothelial cell monolayers were grown on collagenized polyester inserts in the presence of ASC-CM or NHDF-CM in the lower chamber. Fluorescent dye was loaded on the top of the insert, on which endothelial cells were grown. Fluorescence of the lower chamber was measured. Referring now to FIG. 14, reduction of the fluorescence level in ASC-CM treated cells indicated that ASC-CM suppressed $H_2O_2$-induced endothelial cell permeability. To further characterize ASC-CM-mediated stabilization of endothelial barrier, transendothelial electrical resistance (TER) was assessed (FIG. 15). Referring now to FIG. 16, endothelial cells grown on gold electrodes were pretreated with ASC-CM or NHDF-CM; then stimulated with $H_2O_2$. Control monolayers responded to $H_2O_2$ with marked reduction of TER, which was restored within 3 h period. NHDF-CM-pretreated monolayers displayed similar response curve, whereas TER reduction in ASC-CM-pretreated monolayers was significantly attenuated. Referring now to FIG. 17, immunofluorescent analysis of endothelial cells without any treatment showed that $H_2O_2$ caused marked rearrangement of actin cytoskeleton along with the distortion of junctional organization and gap formation in endothelial monolayers. ASC-CM pretreated endothelial cells displayed reduced actin cytoskeleton rearrangement and attenuated gap formation. Referring now to FIGS. 19 and 20, ASC-CM's ability to suppress endothelial barrier dysfunction was voided after heat-inactivation. Referring now to FIG. 22 to 24, ASC-CM's ability to suppress endothelial barrier dysfunction was partially lost after the depletion of exosomes via ultracentrifugation. While the flow-through of ASC-CM from 10 kDa, 30 kDa, and 50 kDa cut-off filters had minimal effect on barrier dysfunction (FIGS. 26 and 27), 100 kDa flow-through suppressed barrier dysfunction (FIG. 28).

Figure 18:
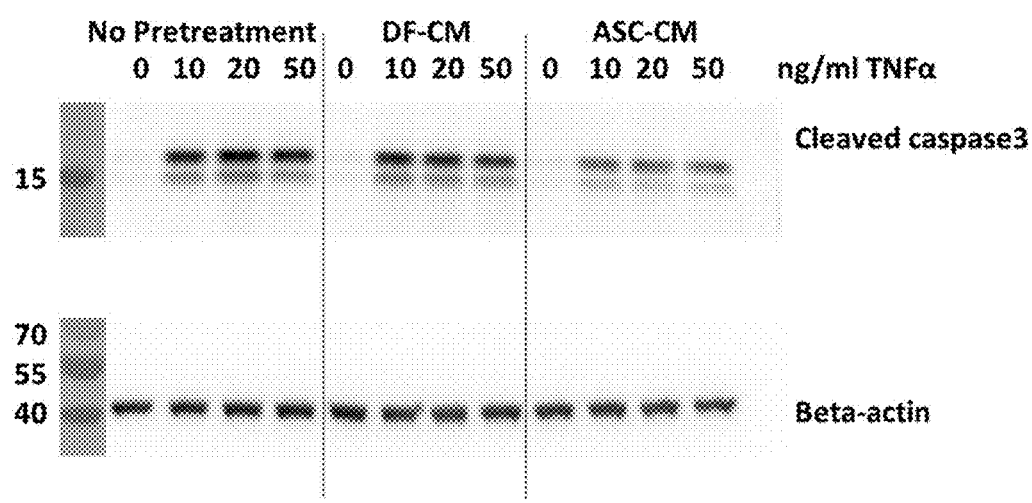
FIG. 18. Western blots of endothelial cells showing the effect of ASC-CM treatment on TNF-α-induced increase in cleaved caspase-3 expression.
Figure 21:
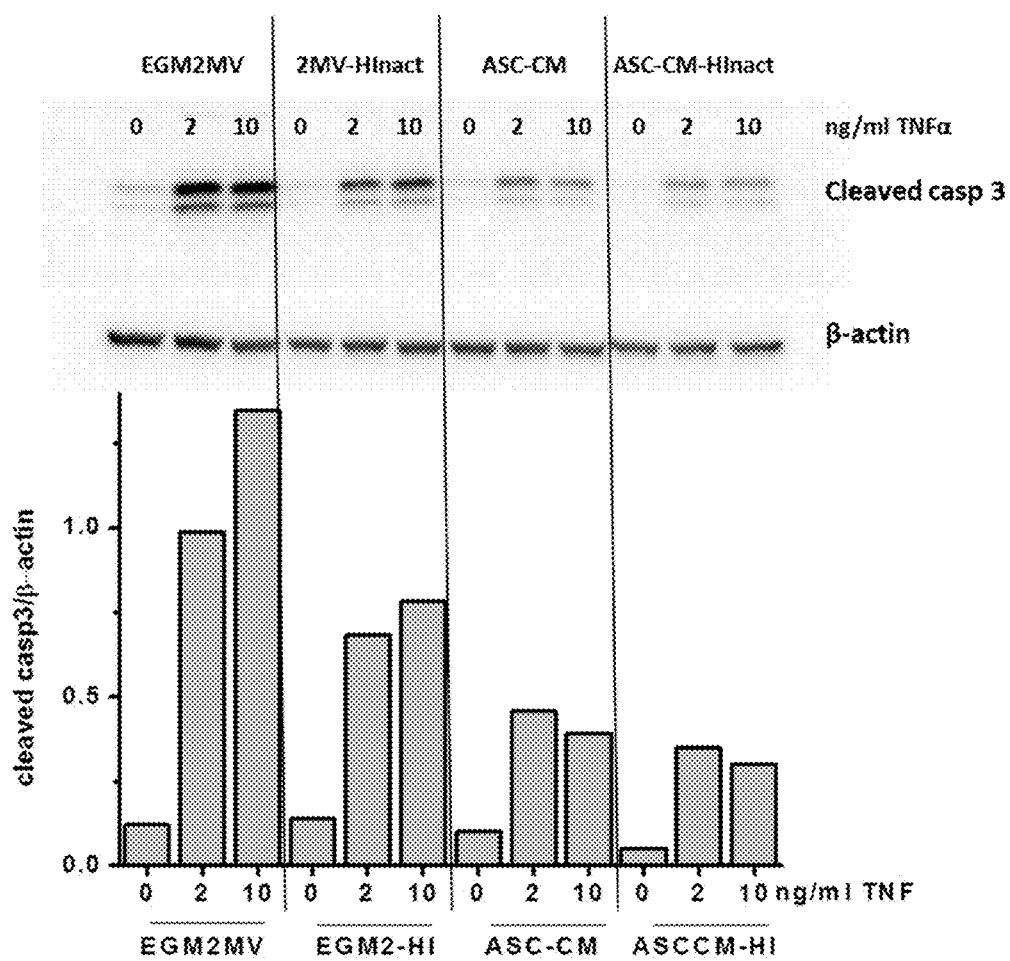
FIG. 21. Western blots of endothelial cells showing the effect of ASC-CM treatment with or without heat-inactivation on TNF-α-induced increase in cleaved caspase-3 expression.
Figure 25:
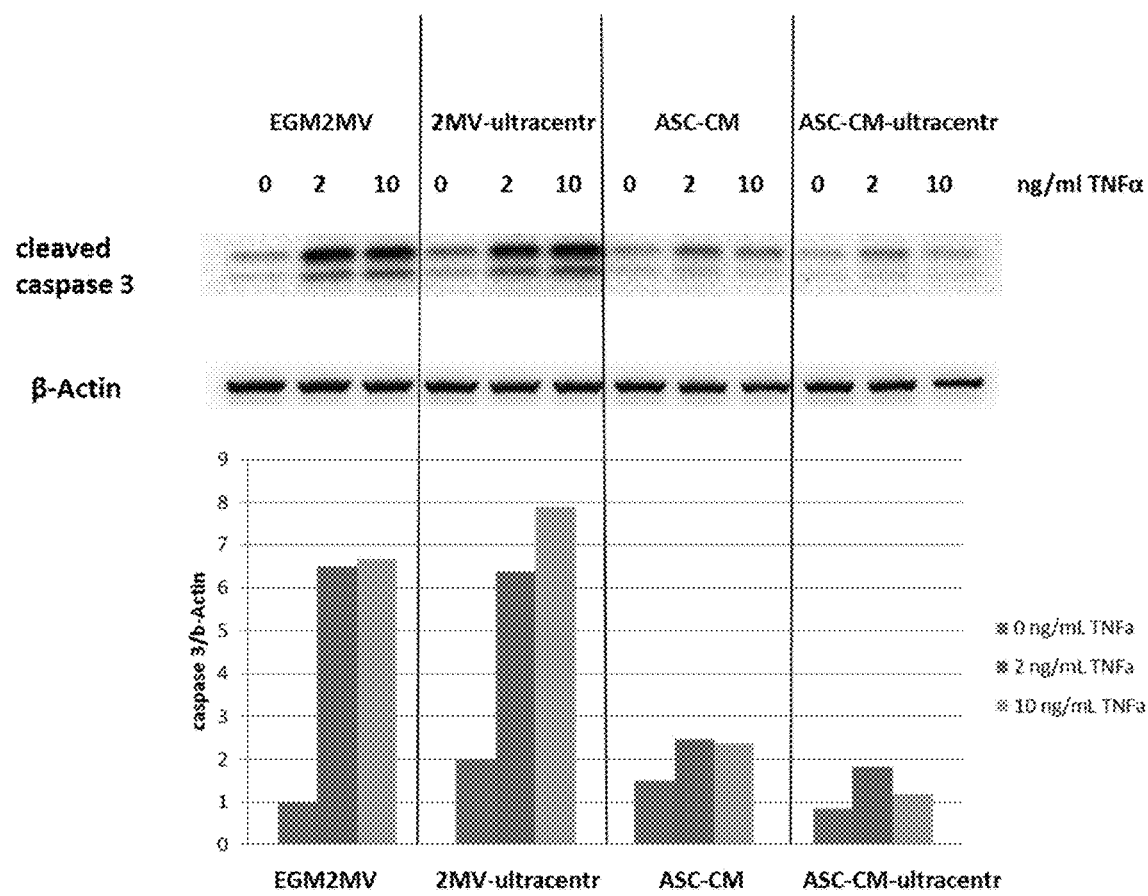
FIG. 25. Western blots of endothelial cells showing the effect of ASC-CM treatment with or without ultracentrifugation on TNF-α-induced increase in cleaved caspase-3 expression.

ASC-CM Effects on Apoptosis in Endothelium. Referring now to FIG. 18, treatment of endothelium with different concentrations of TNF-α increased the expression of cleaved caspase-3. However, ASC-CM pretreatment significantly reduced TNF-α-induced expression of cleaved caspase-3. ASC-CM suppressing pro-apoptotic pathways in endothelium were not heat-sensitive (FIG. 21). Further, depletion of exosomes did not affect ASC-CM's ability to suppress proapoptotic pathways (FIG. 25).

Figure 29:
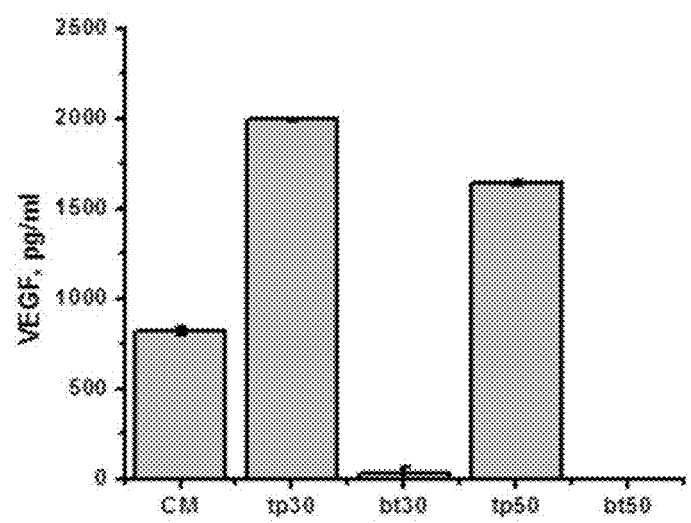
FIG. 29. Bar graph illustrating the effect on the level of VEGF upon treatment with the fractions of ASC-CM with 30 kDa and 50 kDa cut-off filters.
Figure 30:
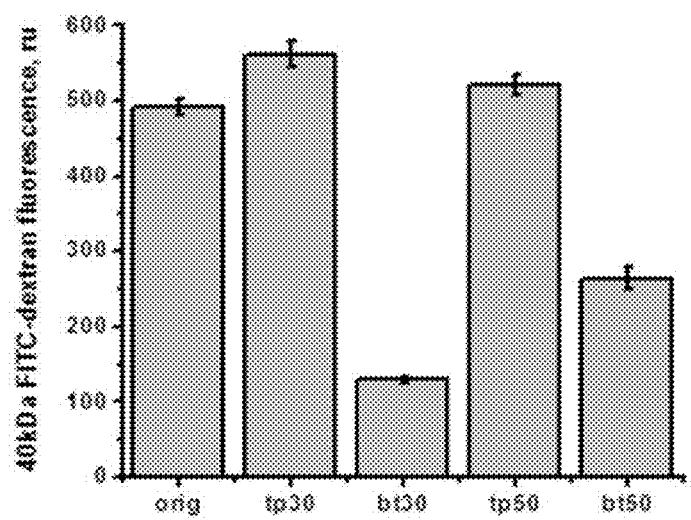
FIG. 30. Bar graph illustrating the effect on the level of 40 kDa FITC-dextran upon treatment with the fractions of ASC-CM with 30 kDa and 50 kDa cut-off filters.
Figure 31:
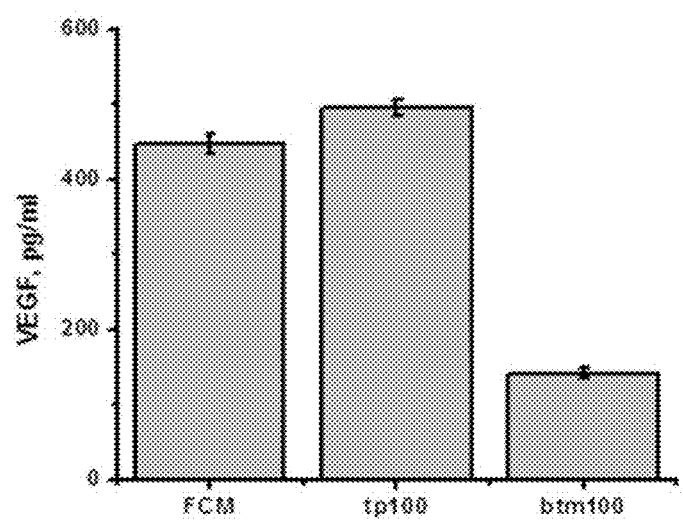
FIG. 31. Bar graph illustrating the effect on the level of VEGF upon treatment with the fractions of ASC-CM with 100 kDa cut-off filter.

Referring now to FIGS. 29 to 31, fractions of ASC-CM with 30 kDa, 50 kDa and 100 kDa cut-off filters showed 27 kDa VEGF partitioning with higher molecular weight.

Figure 32:
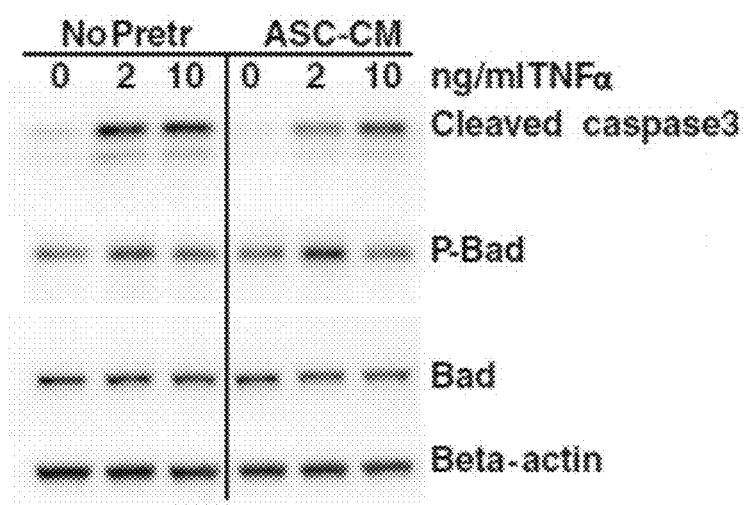
FIG. 32. Western blots of endothelial cells showing the effect of ASC-CM treatment with or without ultracentrifugation on TNF-α-induced increase in cleaved caspase-3 expression. Cell lysates were analyzed with antibodies to cleaved caspase 3, Bad, phospho-Bad and Bim. β-actin staining was used as loading control.
Figure 33:
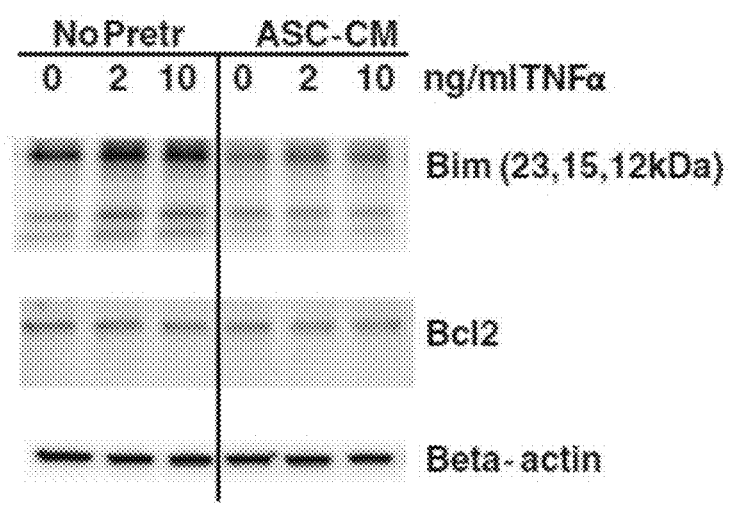
FIG. 33. Western blots of endothelial cells showing the effect of ASC-CM treatment with or without ultracentrifugation on TNF-α-induced increase in cleaved caspase-3 expression. Cell lysates were analyzed with antibodies to cleaved Bim and Bcl2. β-actin staining was used as loading control.

Referring now to FIGS. 32 to 33, to elucidate whether anti-inflammatory effects of hASCCM are mediated by the suppression of pro-apoptotic changes in endothelium, the level of caspase-3 cleavage in response to TNFα were measured. TNFα induced cleavage and activation of caspase-3 evident at 4 h. HPAEC pretreated with hASC-CM showed a marked reduction of cleaved caspase-3 level in response to TNFα. As caspases activation is known to be regulated by pro-apoptotic and anti-apoptotic members of Bcl2 family, the levels of these proteins are affected by hASC secreted factors were measured (FIG. 33). Levels of anti-apoptotic protein Bcl2 and pro-apoptotic protein Bad did not change in HPAEC preconditioned with hASC-CM. No increase in Bad phosphorylation (evident of Bad deactivation) was observed in response to hASC-CM pretreatment (FIG. 32). However, exposure to hASC-secreted factors markedly reduced the level of pro-apoptotic protein Bim.

Figure 34:
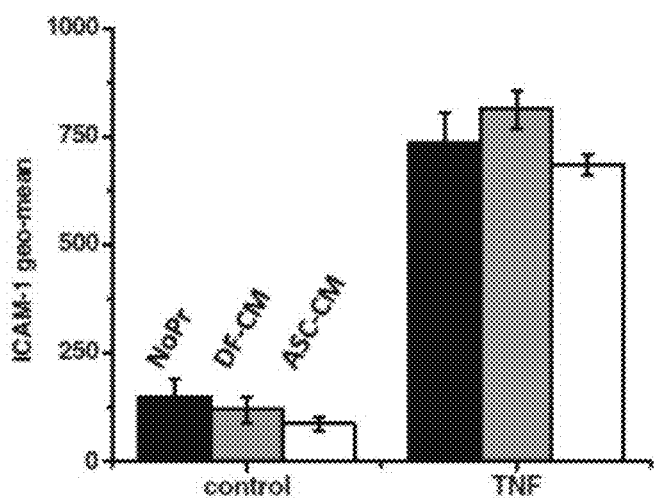
FIG. 34. Bar graph showing the level of ICAM-1 in HPAEC that were pretreated with vehicle control (NoPr, black bars), NHCF-CM (DF-CM, grey bars), and hASC-CM (ASC-CM, white bars), and then stimulated with vehicle or 1 ng/ml TNF-α (4 h).
Figure 35:
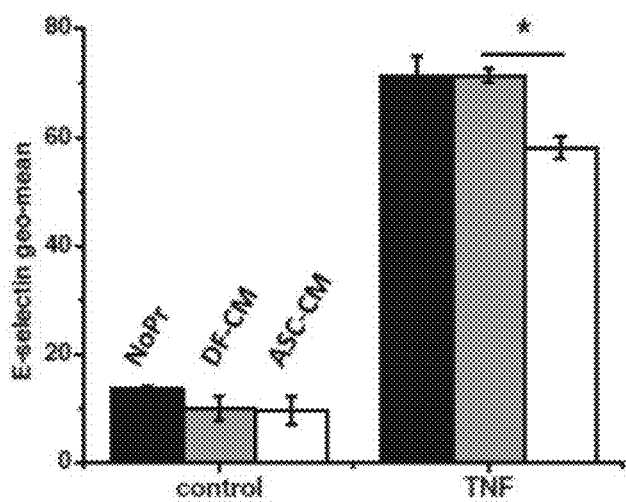
FIG. 35. Bar graph showing the level of E-selectin in HPAEC that were pretreated with vehicle control (NoPr, black bars), NHCF-CM (DF-CM, grey bars), and hASC–

Referring now to FIGS. 34 to 37, to ascertain whether hASC-CM anti-inflammatory effect is dependent on the suppression of endothelial expression of leucocyte receptors, the level of expression of VCAM, ICAM-1, and E-selectin in naïve and TNFα-stimulated HPAEC were measured. Low percentage of unstimulated cells appeared positive for VCAM (data not shown) and E-selectin (FIG. 37), whereas expression of ICAM-1 was detected in at least 70% cells (FIG. 36). TNFα caused dramatic increase in the percentage of VCAM (data not shown) and E-selectin-positive cells, also increasing ICAM-1 expression evident by the shift in ICAM-1 geo-mean value (FIG. 34). HPAEC exposed to hASC-CM did not show significant difference in the expression of VCAM either in absence or presence of TNFα (data not shown). Percentage of ICAM-positive cells detected in the absence of TNFα was significantly suppressed by hASC-CM treatment; however, this effect was not detected in the presence of TNFα. On the contrary, E-selectin expression (evident by geo-mean) was significantly suppressed in the presence of TNFα (FIG. 35).

This study demonstrates that similar to ASC, ASC-CM administration reduces indices of the lung injury in the LPS-induced ARDS model. Although ASC can be easily isolated from liposuction material within hours of the patient admission to ICU (14), the ability to avoid the procedure and use "off-the-shelf" therapeutic product can be a significant advantage for the treatment of critically ill patient. Another advantage is that cell-free ASC-CM is not likely to cause concerns associated with the possibility of the stem cell homing toward pre-existing tumors (36). Therefore, the studies aimed to explore whether ASC-CM can be used as a valid therapeutic material for the treatment of ARDS. In particular, the studies assessed whether a single administration of ASC-CM would have similar potency as a single administration of ASC in the limitation of LPS-induced lung injury.

As discussed herein, a single administration of ASC-CM suppressed ARDS by limiting lung inflammatory histological changes, protein extravasation to airspaces, secretion of inflammatory mediator TNFα in BALF, and the ability of BALF WBC to generate ROS. It was observed that contrary to the effect of ASC administration, ASC-CM-mediated suppression of LPS-induced neutrophil infiltration did not reach significant level 48 h post-injection. It may be that injection of stem cells, if retained lung for a sustained period of time, could elicit more profound effects than a single bolus injection of the beneficiary cell-secreted factors. Nonetheless, the data clearly demonstrate that the ability of neutrophils to cause damage to the parenchyma and epithelium via an oxidative burst is markedly attenuated in the mice receiving ASC-CM. Moreover, our in vitro data show that the ability of endothelium to resist $H_2O_2$-induced barrier dysfunction is enhanced by prolonged exposure to ASC secreted factors. Altogether, our data suggest that ASC-CM is a valid therapeutic product for ARDS treatment, although optimization of the therapy is required to achieve sustained beneficial effect.

In the model used herein, a single delivery of the therapeutic product ASC showed superior potency to ASC-CM, except when protein extravasation in BALF was analyzed. Without being limited by any explanation, increased protein extravasation is the result of the leaky epithelial barrier, which is likely to be counteracted by ASC-secreted factors similar to the effect shown on endothelium. Surprisingly, a markedly beneficial effect of ASC on LPS-induced protein extravasation was not seen. In this regard, one has to consider that the balance of factors secreted by ASC implanted to inflamed tissue may differ from the balance of factors secreted by the "quiescent" ASC in vitro and collected as ASC-CM. Interestingly, the results show that ASC–CM treatment causes marked reduction of LPS-induced VEGF level in BALF, whereas ASC treatment insignificantly increases this level. Without being limited by any explanation, it may be that the secretion of the VEGF by ASC themselves might contribute to the observed fluctuation of the VEGF level. Secretion of VEGF into the airspace may facilitate long-term epithelial repair, but indeed may temporarily contribute to a greater compromise of endothelial as well as epithelial barrier. Therefore, the effect of ASC on ARDS should be seen as complex in nature, making it advantageous to analyze temporal factors in order to optimize this therapy.

Accordingly, time dependence of ASC retention in lung upon intravenous delivery was analyzed. Abundant data of literature show that this route renders preferential cell retention in lung immediately after injection (26, 27, 37). This suggests to follow questions whether ASC are still present in lung at the moment when beneficial effects are observed, namely 48 h post-injection. This also made it interesting to compare the distribution of cells to naïve and LPS-challenged lungs, as well as other internal organs and brain. The former information directly relates to the development and optimization of ARDS therapy; whereas the latter information is of utmost importance for the physicians considering ASC application for the inflammatory pathological conditions of the other organs.

It was observed that approximately 10% of injected ASC are retained in the healthy lung immediately after delivery. This number was somewhat lower than the one reported in literature (26), although the number of cell per injection, the animal model, and the method of detection probably affected the outcome of analysis. It was also observed that LPS-primed lung retained approximately half of the amount of ASC found in the healthy lung within the first 2 h after injection. This might be due to the fact that locally distributed LPS caused temporary pulmonary vasorelaxation. Lungs were shown to decrease the retention of 15-20μ particles in response to sodium nitrorpusside (27). Although systemic delivery of LPS is well-linked to an increase in pulmonary artery pressure (38, 39), intra-tracheal LPS administration shows disparate effect on pulmonary hemodynamics (40). Therefore, it is not surprising that injected ASC manifest different retention rates in lung challenged with LPS.

24 h after LPS/saline and ASC administration, control lung demonstrated marked reduction of the stem cell level, whereas LPS-challenged lung retained the cell level similar to observed before. Importantly, 48 h post-injection, LPS-challenged lungs still showed the presence of stem cells, suggesting that the inflammation contributes to the sustained retention of the ASC. In our experiment, ~3% of the initial ASC dose were retained in the lung 48 h after injection, which was consistent with the data of others showing ~1% retention after 72 h (15). The fact that the substantial amount of ASC (≥½ of the amount engrafted within 2 h of injection) was present in ARDS lung for at least 48 h following cell injection suggested that stem cell therapy is not likely to require frequent re-administration to yield sustained ARDS suppression.

Dissimilar to lung, other organs showed only minor retention of ASC following IV delivery. These data suggest that when direct organ targeting is preferential, cell may need to be delivered in the respective artery rather than vein. On the other hand, increase in mortality was shown when stem cells were delivered in the left atrium, possibly due to the embolism of cardiac circulation (26). It did not to detect re-distribution of ASC to spleen or liver, as shown in other reports (41). Possible re-distribution to the thoracic lymph nodes (24) was not analyzed here.

Low percentage of stem cell engraftment in lung comparing to the original delivered dose led others to speculate that the effect on ARDS is mostly paracrine (15), mediated by the factors secreted by stem cells engrafted elsewhere. Although it cannot be completely exclude this possibility, our data show that the time-dependent curves of ASC distribution in other organs follow the time-dependent curve of ASC distribution in lung, with the higher cell level in the first 2 h following injection, and decrease in the following 48 h. Our data clearly show that ARDS lung is the only organ which harbors substantial amount of ASC 48 h post-injection, making pulmonary-engrafted ASC the primary source of the therapeutic material. Therefore, the effect of stem cell therapy on lung is likely to be driven by both cellular (mitochondrial transfer) and paracellular (secreted factors) mechanisms. Whereas secreted factor therapy by ASC-CM can be sufficient to limit ARDS, continuous delivery of ASC-CM can yield more pronounced results than bolus injection used in this study.

REFERENCES

1. Boyle A J, Sweeney R M, McAuley D F. Pharmacological treatments in ARDS; a state-of-the-art update. BMC medicine. 2013;11(1):166.
2. Force A D T, Ranieri V M, Rubenfeld G D, Thompson B T, Ferguson N D, Caldwell E, et al. Acute respiratory distress syndrome: the Berlin Definition. JAMA: the journal of the American Medical Association. 2012;307 (23):2526-33.
3. Rubenfeld G D. Epidemiology of acute lung injury. Crit Care Med. 2003;31(4 Suppl):S276-84.
4. Fanelli V, Vlachou A, Ghannadian S, Simonetti U, Slutsky A S, Zhang H. Acute respiratory distress syndrome: new definition, current and future therapeutic options. Journal of thoracic disease. 2013;5(3):326-34.
5. Hayes M, Curley G, Laffey J G. Mesenchymal stem cells—a promising therapy for Acute Respiratory Distress Syndrome. F1000 Med Rep. 2012;4:2.
6. Sueblinvong V, Weiss D J. Stem cells and cell therapy approaches in lung biology and diseases. Transl Res. 2010;156(3):188-205.
7. Danchuk S. Ylostalo J H, Hossain F, Sorge R, Ramsey A. Bonvillain R W, et al. Human multipotent stromal cells attenuate lipopolysaccharide-induced acute lung injury in mice via secretion of tumor necrosis factor-alpha-induced protein 6. Stem Cell Res Ther. 2011 2(3):27.
8. Gupta N, Su X, Popov B, Lee J W, Serikov V, Matthay M A. Intrapulmonary delivery of bone marrow-derived mesenchymal stem cells improves survival and attenuates endotoxin-induced acute lung injury in mice. J Immunol. 2007;179(3): 1855-63.
9. Lee J W, Fang X, Gupta N, Serikov V, Matthay M A. Allogeneic human mesenchymal stem cells for treatment of E. coli endotoxin-induced acute lung injury in the ex vivo perfused human lung. Proc Natl Acad Sci USA. 2009;106(38):16357-62.
10. Krasnodembskaya A, Song Y, Fang X, Gupta N, Serikov V, Lee J W, et al. Antibacterial effect of human mesenchymal stem cells is mediated in part from secretion of the antimicrobial peptide LL-37. Stem Cells. 2010;28(12): 2229-38.
11. Mei S H, McCarter S D, Deng Y, Parker C H, Liles W C, Stewart D J. Prevention of LPS-induced acute lung injury in mice by mesenchymal stem cells overexpressing angiopoietin 1. PLoS Med. 2007;4(9):e269.
12. Nemeth K, Leelahavanichkul A, Yuen P S, Mayer B, Parmelee A, Doi K, et al. Bone marrow stromal cells attenuate sepsis via prostaglandin E(2)-dependent reprogramming of host macrophages to increase their interleukin-10 production. Nat Med. 2009;15(1):42-9.
13. Ortiz L A, Dutreil M. Fattman C, Pandey A C, Torres G, Go K, et al. Interleukin 1 receptor antagonist mediates the antiinflammatory and antifibrotic effect of mesenchymal stem cells during lung injury. Proc Natl Acad Sci USA. 2007;104(26):11002-7.
14. Strioga M, Viswanathan S, Darinskas A, Slaby O, Michalek J. Same or not the same? Comparison of adipose tissue-derived versus bone marrow-derived mesenchymal stem and stromal cells. Stem cells and development. 2012;21(14):2724-52.

15. Chien M H, Bien M Y, Ku C C, Chang Y C, Pao H Y, Yang Y L, et al. Systemic human orbital fat-derived stem/stromal cell transplantation ameliorates acute inflammation in lipopolysaccharide-induced acute lung injury. Crit Care Med. 2012;40(4):1245-53.
16. Shin S, Kim Y, Jeong S, Hong S, Kim I, Lee W, et al. The therapeutic effect of human adult stem cells derived from adipose tissue in endotoxemic rat model. International journal of medical sciences. 2013;10(1):8-18.
17. Zhang S, Danchuk S D, Bonvillain R W, Xu B, Scruggs B A, Strong A L, et al. Interleukin 6 mediates the therapeutic effects of adipose-derived stromal/stem cells in lipopolysaccharide-induced acute lung injury. Stem Cells. 2014.
18. Zhang S, Danchuk S D, Imhof K M, Semon J A, Scruggs B A, Bonvillain R W, et al. Comparison of the therapeutic effects of human and mouse adipose-derived stem cells in a murine model of lipopolysaccharide-induced acute lung injury. Stem Cell Res Ther. 2013;4(1):13.
19. Chang C L, Leu S, Sung H C, Zhen Y Y, Cho C L, Chen A, et al. Impact of apoptotic adipose-derived mesenchymal stem cells on attenuating organ damage and reducing mortality in Rat sepsis syndrome induced by cecal puncture and ligation. J Transl Med. 2012;10:244.
20. Liang Z D, Yin X R, Cai D S, Zhou H, Pei L. Autologous transplantation of adipose-derived stromal cells ameliorates ventilator-induced lung injury in rats. J Transl Med. 2013;11(1):179.
21. Sun C K, Yen C H, Lin Y C, Tsai T H, Chang L T, Kao Y H, et al. Autologous transplantation of adipose-derived mesenchymal stem cells markedly reduced acute ischemia-reperfusion lung injury in a rodent model. J Transl Med. 2011;9:118.
22. Xu J, Qu J, Cao L, Sai Y, Chen C, He L. et al. Mesenchymal stem cell-based angiopoietin-1 gene therapy for acute lung injury induced by lipopolysaccharide in mice. The Journal of pathology. 2008;214(4):472-81.
23. Dooner M S, Aliotta J M, Pimentel J, Dooner G J, Abedi M. Colvin G, et al. Conversion potential of marrow cells into lung cells fluctuates with cytokine-induced cell cycle. Stem cells and development. 2008;17(2):207-19.
24. Islam M N, Das S R, Emin M T, Wei M, Sun L, Westphalen K, et al. Mitochondrial transfer from bone-marrow-derived stromal cells to pulmonary alveoli protects against acute lung injury. Nat Med. 2012;18(5):759-65.
25. Lee S H, Lee E J, Lee S Y, Kim J H. Shim J J, Shin C, et al. The effect of adipose stem cell therapy on pulmonary fibrosis induced by repetitive intratracheal bleomycin in mice. Experimental lung research. 2014;40(3):117-25.
26. Elhami E, Dietz B, Xiang B, Deng J, Wang F, Chi C, et al. Assessment of three techniques for delivering stem cells to the heart using PET and MR imaging. EJNMMI research. 2013;3(1):72.
27. Schrepfer S, Deuse T, Reichenspurner H, Fischbein M P, Robbins R C, Pelletier M P. Stem cell transplantation: the lung barrier. Transplantation proceedings. 2007;39(2):573-6.
28. Zheng G, Huang L, Tong H, Shu Q, Hu Y, Ge M, et al. Treatment of acute respiratory distress syndrome with allogeneic adipose-derived mesenchymal stem cells: a randomized, placebo-controlled pilot study. Respir Res. 2014;15(1):39.
29. Tatsumi K, Ohashi K, Matsubara Y, Kohori A, Ohno T, Kakidachi H, et al. Tissue factor triggers procoagulation in transplanted mesenchymal stem cells leading to thromboembolism. Biochemical and biophysical research communications. 2013.
30. Forde A, Constien R, Grone H J, Hammerling G, Arnold B. Temporal Cre-mediated recombination exclusively in endothelial cells using Tie2 regulatory elements. Genesis (New York, N.Y.: 2000). 2002;33(4):191-7.
31. Traktuev D O, Merfeld-Clauss S, Li J, Kolonin M, Arap W, Pasqualini R, et al. A population of multipotent CD34-positive adipose stromal cells share pericyte and mesenchymal surface markers, reside in a periendothelial location, and stabilize endothelial networks. Circulation research. 2008;102(1):77-85.
32. Sroussi H Y, Lu Y, Zhang Q L, Villines D, Marucha P T. S100A8 and S100A9 inhibit neutrophil oxidative metabolism in-vitro: involvement of adenosine metabolites. Free radical research. 2010;44(4):389-96.
33. Bogatcheva N V, Adyshev D, Mambetsariev B, Moldobaeva N, Verin A D. Involvement of microtubules, p38, and Rho kinases pathway in 2-methoxyestradiol-induced lung vascular barrier dysfunction. Am J Physiol Lung Cell Mol Physiol. 2007;292(2):L487-99.
34. Houlihan D D, Mabuchi Y, Morikawa S, Niibe K, Araki D. Suzuki S, et al. Isolation of mouse mesenchymal stem cells on the basis of expression of Sca-1 and PDGFR-alpha. Nature protocols. 2012;7(12):2103-11.
35. Bourin P. Bunnell B A, Casteilla L, Dominici M, Katz A J, March K L, et al. Stromal cells from the adipose tissue-derived stromal vascular fraction and culture expanded adipose tissue-derived stromal/stem cells: a joint statement of the International Federation for Adipose Therapeutics and Science (IFATS) and the International Society for Cellular Therapy (ISCT). Cytotherapy. 2013; 15(6):641-8.
36. Klopp A H, Zhang Y, Solley T, Amaya-Manzanares F, Marini F, Andreeff M, et al. Omental adipose tissue-derived stromal cells promote vascularization and growth of endometrial tumors. Clinical cancer research: an official journal of the American Association for Cancer Research. 2012;18(3):771-82.
37. Yukawa H, Watanabe M, Kaji N, Okamoto Y, Tokeshi M, Miyamoto Y, et al. Monitoring transplanted adipose tissue-derived stem cells combined with heparin in the liver by fluorescence imaging using quantum dots. Biomaterials. 2012;33(7):2177-86.
38. Chlopicki S, Walski M, Bartus J B. Ultrastructure of immediate microvascular lung injury induced by bacterial endotoxin in the isolated, no-deficient lung perfused with full blood. Journal of physiology and pharmacology: an official journal of the Polish Physiological Society. 2005; 56 Suppl 4:47-64.
39. Kreil E A, Greene E, Fitzgibbon C, Robinson D R, Zapol W M. Effects of recombinant human tumor necrosis factor alpha, lymphotoxin, and *Escherichia coli* lipopolysaccharide on hemodynamics, lung microvascular permeability, and eicosanoid synthesis in anesthetized sheep. Circulation research. 1989;65(2):502-14.
40. Lorenzoni A G, Wideman R F, Jr. Intratracheal administration of bacterial lipopolysaccharide elicits pulmonary hypertension in broilers with primed airways. Poultry science. 2008;87(4):645-54.
41. Wang N, Shao Y, Mei Y, Zhang L, Li Q, Li D, et al. Novel mechanism for mesenchymal stem cells in attenuating peritoneal adhesion: accumulating in the lung and secreting tumor necrosis factor alpha-stimulating gene-6. Stem Cell Res Ther. 2012;3(6):51.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

The invention claimed is:

1. A method for treating a patient, comprising the step of: administering to a patient at least one therapeutically effective dose of an agent comprising adipose-derived Adult Stem Cell-Conditioned Media, wherein the adipose-derived Adult Stem Cell-Conditioned Media is derived from adipose-derived Adult Stem Cells that are negative for CD31 and CD45,
wherein the patient is afflicted with Adult Respiratory Distress Syndrome caused by inflammation and barrier hyperpermeability, and wherein the patient is selected from the group consisting of: human and animal.

2. The method according to claim 1, wherein the Adult Respiratory Distress Syndrome is caused by an upper respiratory tract infection caused by at least one coronavirus selected from the group consisting of: Severe Acute Respiratory Syndrome coronavirus and Middle East Respiratory Syndrome coronavirus.

3. The method according to claim 1, where the therapeutically effective dose of the agent is administered intravenously.

4. The method according to claim 1, wherein the patient is administered a therapeutically effective dose of the adipose-derived Adult Stem Cell-Conditioned Media, the adipose-derived Adult Stem Cell-Conditioned Media comprising material have a molecular weight of greater than about 10,000 Daltons.

5. The method according to claim 4, wherein the adipose-derived Adult Stem Cell-Conditioned Media is administered intravenously.

6. The method according to claim 4, wherein the adipose-derived Adult Stem Cell-Conditioned Media is administered by aspirating the material into at least one lung of the patient.

7. The method according to claim 5, wherein the dose of the adipose-derived Adult Stem Cell-Conditioned Media administered intravenously is about 0.1ml/kg to about 2.0 ml/kg, of 100× concentrate of the adipose-derived Adult Stem Cell-Conditioned Media.

8. The method according to claim 5, wherein the dose of the adipose-derived Adult Stem Cell-Conditioned Media administered intravenously is about 0.5ml/kg to about 1.0 ml/kg, of 100× concentrate of the adipose-derived Adult Stem Cell-Conditioned Media.

9. The method according to claim 4, further comprising the step of formulating the adipose-derived Adult Stem Cell-Conditioned Media material to avoid heat sensitivity.

10. The method according to claim 4, further comprising the step of formulating the adipose-derived Adult Stem Cell-Conditioned Media material to avoid exosome sensitivity.

11. The method according to claim 1, wherein the patient is administered a therapeutically effective dose of the adipose-derived Adult Stem Cell-Conditioned Media, the adipose-derived Adult Stem Cell-Conditioned Media comprising material have a molecular weight of greater than about 50,000 Daltons.

12. The method according to claim 1, wherein the patient is administered a therapeutically effective dose of the adipose-derived Adult Stem Cell-Conditioned Media, the adipose-derived Adult Stem Cell-Conditioned Media comprising material have a molecular weight of greater than about 60,000 Daltons.

13. The method according to claim 1, wherein the patient is administered a therapeutically effective dose of the adipose-derived Adult Stem Cell-Conditioned Media, the adipose-derived Adult Stem Cell-Conditioned Media comprising material have a molecular weight of greater than about 70,000 Daltons.

14. The method according to claim 1, wherein the patient is administered a therapeutically effective dose of the adipose-derived Adult Stem Cell-Conditioned Media, the adipose-derived Adult Stem Cell-Conditioned Media comprising material have a molecular weight of greater than about 80,000 Daltons.

15. The method according to claim 1, wherein the patient is administered a therapeutically effective dose of the adipose-derived Adult Stem Cell-Conditioned Media, the adipose-derived Adult Stem Cell-Conditioned Media comprising material have a molecular weight of greater than about 100,000 Daltons.

16. The method according to claim 1, wherein the patient is administered a therapeutically effective dose of the adipose-derived Adult Stem Cell-Conditioned Media, the adipose-derived Adult Stem Cell-Conditioned Media comprising material have a molecular weight of greater than about 150,000 Daltons.

17. The method according to claim 1, wherein the patient is administered a therapeutically effective dose of a fraction of the adipose-derived Adult Stem Cell-Conditioned Media, comprised of exosomes.

18. The method according to claim 1, wherein the patient is administered a therapeutically effective dose of a fraction of the adipose-derived Adult Stem Cell-Conditioned Media, comprised of exosomes concentrated by any of filtration, centrifugation, or precipitation and resuspension.

19. The method according to claim 1, wherein the inflammation and barrier hyperpermeability are induced by gram-negative bacterial infection or endotoxin.

20. A method of suppressing inflammation and barrier hyperpermeability, comprising providing a subject at least one therapeutically effective dose of an agent comprising adipose-derived Adult Stem Cell-Conditioned Media, wherein the adipose-derived Adult Stem Cell-Conditioned Media is adipose-derived Adult Stem Cell-Conditioned Media derived from adipose-derived Adult Stem Cells that are negative for CD31 and CD45.

21. The method according to claim 20, wherein the subject comprises a human, an animal, a cell, or a tissue.

* * * * *